(12) United States Patent
Carcy et al.

(10) Patent No.: US 7,722,879 B2
(45) Date of Patent: May 25, 2010

(54) BABESIA VACCINES

(75) Inventors: Bernard Piere Dominique Carcy, Montpellier (FR); Andre Francois Gorenflot, Montpellier (FR); Theodorus Petrus Maria Schetters, Cuyk (NL); Prisca Laetitia Cibrelus, Montpellier (FR); Karina Moubri, Mauguio (FR); Delphine Depoix, Tours (FR)

(73) Assignee: Intervet International B.V., Boxmeer (NL)

( * ) Notice: Subject to any disclaimer, the term of this patent is extended or adjusted under 35 U.S.C. 154(b) by 389 days.

(21) Appl. No.: 10/563,601

(22) PCT Filed: Jul. 12, 2004

(86) PCT No.: PCT/EP2004/051454

§ 371 (c)(1),
(2), (4) Date: May 4, 2006

(87) PCT Pub. No.: WO2005/012343

PCT Pub. Date: Feb. 10, 2005

(65) Prior Publication Data

US 2007/0041991 A1    Feb. 22, 2007

(30) Foreign Application Priority Data

Jul. 10, 2003    (EP)    ................... 03077178

(51) Int. Cl.
*A61K 39/02*    (2006.01)
(52) U.S. Cl. ................................. 424/190.1
(58) Field of Classification Search ................ None
See application file for complete search history.

(56) References Cited

FOREIGN PATENT DOCUMENTS

| EP | 0 417 524 A1 | 3/1991 |
| EP | 1 050 541 A1 | 11/2000 |
| EP | 1 238 983 A1 | 9/2002 |
| WO | WO0177384 | * 10/2001 |

OTHER PUBLICATIONS

Gerhold et al [BioEssays, vol. 18, pp. 973-981 {1996}].*
Burgess et al., The Journal of Cell Biology, 111:2129-2138, 1990.*
Bowie et al (Science, 1990, 247:1306-1310.*
Vaccines W.B. Saunders Company, 1988, p. 571.*
Vettore et al 2001 Genet. Mol. Biol. vol. 24 (1-4), (1-7).*
Carcy B et al: "A 37-Kilodalton Glycoprotein of Babesia divergens . . . "Infec. & Immun., Amer. Soc. for Micro., Mar. 7, 1995, p. 811-817, vol. 63 No. 3, Washington, US.
Carret Celine et al: "Characterization and molecular . . . ", Eur. J. Biochem, 1999, p. 1015-1021, vol. 265 No. 3, Berlin, DE.
Delbecq S et al: "Babesia divergens . . . ", Parasitology Cambridge Univ. Press, 2002, p. 305-312, vol. 125 No. 4, London, GB.
Fukumoto, S et al "Identification and expression of a 50-kilodalton surface antigen of Babesia gibsoni . . . " J. of Clinical Microbiology, Jul. 2001, p. 2603-2609,vol. 39, No. 7.

* cited by examiner

*Primary Examiner*—Robert B Mondesi
*Assistant Examiner*—Nina A Archie
(74) *Attorney, Agent, or Firm*—William M. Blackstone; Aaron L. Schwartz

(57) ABSTRACT

The invention relates to *Babesia* proteins of a 28kDa protein family and to immunogenic fragments of such proteins, to nucleic acids encoding such proteins or fragments, to cDNA fragments, recombinant DNA molecules, live recombinant carriers, or host cells comprising such nucleic acids, to vaccines, to methods for the preparation of such vaccines, to the use of such proteins or fragments for the prophylactic or therapeutic treatment of an infection or its clinical signs caused by an organism of the family Babesiidae, and to diagnostic tests for detection of nucleic acids, antibodies or antigens of an organism of the family Babesiidae.

9 Claims, 19 Drawing Sheets

Figure 1

Figure 5:
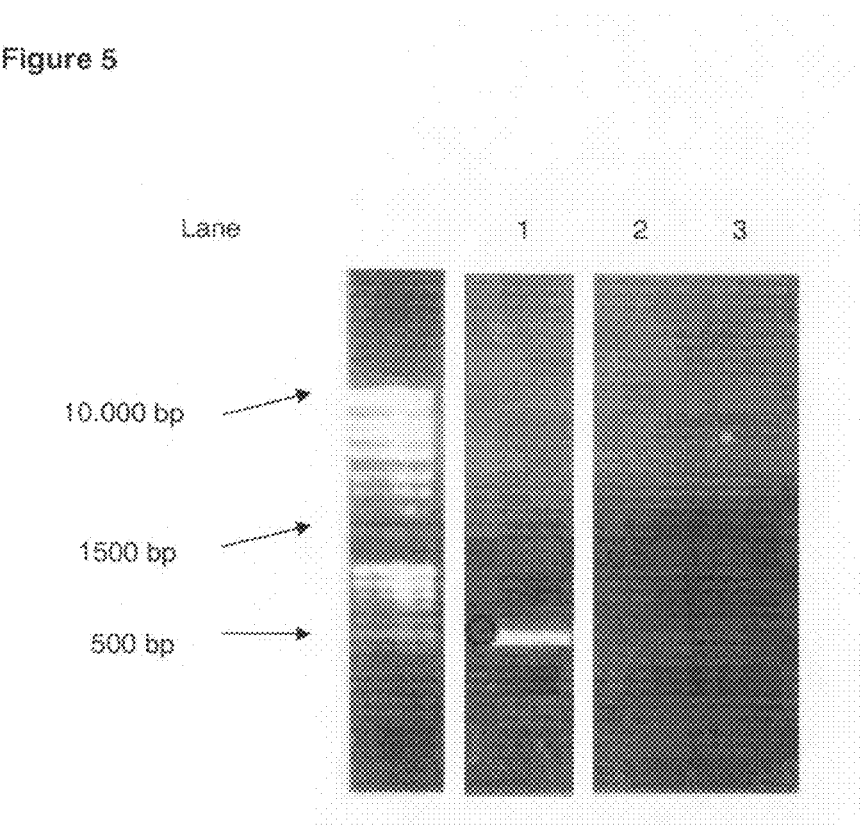

```
Bc28.2    MKGFFGIILSIIFVRAVSCTEDENRDSVVEGATSVEASLKEQIDWLAERYSADLTNKDTS 60
Bc28.1    MKGFFGIILSIIFVRAVSCTEDEKRDSVVEGATSVEASLKEQIDWLAERYSADLTNKDTS 60
          **********************:*************************************
                                ↑

Bc28.2    KWNTEEQVKELLNEKAVGIESRLLAIAKEFHKLKSVLCTGVNETPAHVANRVSPGDAISM 120
Bc28.1    KWNTDEKVKELLNEKAVGIESRLLAIAKEFHKLKSVLCTGVNETPAHVANRVSPGDAISM 120
          ****:*:*****************************************************

Bc28.2    LYVLPNTHRELSSLKNKIDEWKKVKASDNGTNVIKNIKDDRTNTWFVAHGFKVAELNDVT 180
Bc28.1    LYVLSITHRELSSLKNKIDEWKKVKASEDGTKVIQNIKDDRTNTWFVAHGFKVAELNDVT 180
          ****. ********************::**:**:**************************

Bc28.2    LEKLATVVKKLVSHKDMKYINKVMKKYFDRQKKE-AERLTKKAEKGMSGGKYKVKGY--A 237
Bc28.1    LEKLATVVNELVSHKDMIYINDAMKQNVDKWTKEESERLAMMAEQGISGAKGKKDGFSFA 240
          ********::******* ***..**: .*: .** :***:   **:*:**.* * .*:  *
                                                                    ↑
Bc28.2    APSTWML--------- 244
Bc28.1    GLSVISLLVAAVAVVV 256
          . *. *
```

Figure 2

```
A8       MKGFFGIILSIIFVRAVSCTEDEKRDSVVEGATSVEASLKEQIDWLAERYSADLTNKDTS 60
BcB      MKGFFGIILSIIFVRAVSCTEDEKRDSVVEGATSVEASLKEQIDWLAERYSADLTNKDTS 60
34.01    MKGFFGIILSIIFVRAVSCTEDEKRDTVVEGATSVEASLKEQIDWLAERYSADLTNKDTS 60
BcA      MKGFFGIILSIIFVRAVSCTEDEKRDSVVEGATSVEASLKEQIDWLAERYSADLTNKDTS 60
Robin    MKGFFGIILSIIFVRAVSCTEDEKRDSVVEGATSVEASLKEQIDWLAERYSADLTNKDTS 60
Castres  MKGFFGIILSIIFVRAVSCTEDEKRDSVVEGATSVEASLKEQIDWLAERYSADLTNKDTS 60
         ****************************:******************************

A8       KWNTDEKVKELLNEKAVGIESRLLAIAKEFHKLKSVLCTGVNETPAHVANRVSPGDAISM 120
BcB      KWNTDEQVKELLNEKAVGIESRLLAIAKEFHKLKSVLCTGVNETPAHVANRVSPGDAISM 120
34.01    KWNTNEQVKELLNEKAVGIESRLLAIAKEFHKLKSVLCTGVNETPAHVANRVSPGDAISM 120
BcA      KWNTDEKVKELLNEKAVGIESRLLAIAKEFHKLKSVLCTGVNETPAHVANRVSPGDAISM 120
Robin    KWNTDEKVKELLNEKAVGIESRLLAIAKEFHKLKSVLCTGVNETPAHVANRVSPGDAISM 120
Castres  KWNTDEQVKELLNEKAVGIESRLLAIAKEFHKLKSVLCTGVNETPAHVANRVSPGDAISM 120
         ****:*:*****************************************************

A8       LYVLSITHRELSSLKNKIDEWKKVKASEDGTKVIQNIKDDRTNTWFVAHGFKVAELNDVT 180
BcB      LYVLSITHRELSSLKNKIDEWKKVKASDNGTNVIQNIKDDRTNTWFVAHGFKVAELNDVT 180
34.01    LYVLSITHRELSSLKNKIDEWKKVKASDNGTNVIQNIKDDRTNTWFVAHGFKVAELNDVT 180
BcA      LYVLSITHRELSSLKNKIDEWKKVKASEDGTKVIQNIKDDRTNTWFVAHGFKVAELNDVT 180
Robin    LYVLSITHRELSSLKNKIDEWKKVKASEDGTKVIQNIKDDRTNTWFVAHGFKVAELNDVT 180
Castres  LYVLSITHRELSSLKNKIDEWKKVKASEDGTKVIQNIKDDRTNTWFVAHGFKVAELNDVT 180
         ***************************::**:***************************

A8       LEKLATVVNELVSHKDMIYINDAMKQNVDKWTKEESERLAMMAEQGISGAKGKKDGFSFA 240
BcB      LEKLATVVNELVSHNDMIYINDAMKQNVDKWTKEESERLAMMAEQGISGAKGKKDGFSFA 240
34.01    LEKVATVVNELVSHNDMIYINDAMKQNVDKWNKE-SERLAMMAEQGISGAKGKKDGFSFA 239
BcA      LEKLATVVNELVSHKDMIYINDAMKQNVDKWTKEESERLAMMAEQGISGAKGKKDGFSFA 240
Robin    LEKLATVVNELVSHKDMIYINDAMKQNVDKWTKEESERLAMMAEQGISGAKGKKDGFSFA 240
Castres  LEKLATVVNELVSHNDMIYINDAMKQNVDKWNKE-SERLAMMAEQGISGAKGKKDGFSFA 239
         ***:**********:***************.** *************************

A8       GLSVISLLVAAVAVVV 256
BcB      GLSVISLLVAAVAVVL 256
34.01    GLSVISLLVAAVAVVL 255
BcA      GLSVISLLVAAVAVVV 256
Robin    GLSVISLLVAAVAVVV 256
Castres  GLSVISLLVAAVAVVL 255
         **************:
```

Figure 3

```
                      5'UTR
                                                             Met
Bc28.2    AGTCGATACCTCCGAGAATAGTCTTGTATTAATCCTGTCGCTATTCACAATGAAGGGTTT  60
Bc28.1    AGTCGATACCTCCGAGAATAGTCTTGTATTAATCCTGTCGCTATTCACAATGAAGGGTTT  60
          ************************************************************

Fspe3
Bc28.2    CTTCGGAATTATTTTGTCTATTATTTTCGTTCGTGCCGTTAGCTGCACTGAGGATGAGAA  120
Bc28.1    CTTCGGAATTATTTTGTCCATTATTTTTGTTCGTGCCGTTAGCTGCACTGAGGATGAGAA  120
          ****************** ******* *********************************

Bc28.2    CAGGGATAGTGTCGTCGAGGGCGCTACGTCCGTTGAAGCCAGCTTAAAGGAGCAGATCGA  180
Bc28.1    AAGGGATAGTGTCGTCGAGGGCGCTACGTCCGTTGAAGCCAGCTTAAAGGAGCAGATCGA  180
           ***********************************************************

Bc28.2    CTGGCTCGCTGAACGTTATTCCGCTGACTTGACTAACAAAGACACTTCAAAATGGAATAC  240
Bc28.1    CTGGCTCGCTGAACGTTATTCCGCTGACTTGACTAACAAAGACACTTCAAAATGGAATAC  240
          ************************************************************

Bc28.2    CGAAGAGCAGGTGAAGGAGCTGTTAAATGAGAAGGCTGTTGGCATAGAGTCTCGCCTTCT  300
Bc28.1    CGACGAGAAGGTGAAGGAGCTGTTGAATGAGAAGGCTGTTGGCATAGAGTCTCGCCTTCT  300
          *** *** ***************** **********************************

Bc28.2    TGCCATTGCTAAGGAGTTCCACAAATTGAAGTCCGTTCTGTGCACCGGTGTCAACGAAAC  360
Bc28.1    TGCCATTGCTAAGGAATTCCACAAATTGAAGTCCGTTCTGTGCACCGGCGTCAACGAAAC  360
          *************** ******************************** ***********

Bc28.2    TCCCGCTCATGTCGCTAACAGGGTGTCACCCGGAGACGCCATCTCCATGCTTTACGTGCT  420
Bc28.1    TCCCGCTCATGTCGCTAACAGGGTGTCACCCGGAGACGCCATCTCCATGCTCTACGTGCT  420
          ************************************************* ****** pr 3
Bc28.2    TCCTAACACTCACAGGGAATTGTCTAGCCTTAAGAATAAGATCGATGAATGGAAGAAGGT  480
Bc28.1    TTCTATCACTCACAGGGAATTGTCTAGCCTTAAGAATAAGATCGATGAATGGAAGAAGGT  480
          * *** ******************************************************

Bc28.2    CAAGGCATCTGACAATGGCACCAATGTGATCAAAAATATCAAGGACGACAGGACTAACAC  540
Bc28.1    CAAGGCATCTGAAGATGGCACCAAAGTGATCCAAAATATCAAGGACGACAGGACTAACAC  540
          ************  ********** ****** ****************************

Cons3.1
Bc28.2    CTGGTTCGTTGCCCATGGATTCAAGGTAGCTGAGCTCAACGATGTAACCCTTGAGAAACT  600
Bc28.1    CTGGTTCGTTGCCCATGGATTCAAGGTAGCTGAGCTCAACGATGTCACCCTTGAGAAACT  600
          ********************************************* **************

Bc28.2    TGCAACAGTGGTTAAAAAATTGGTGTCCCACAAAGATATGAAATACATTAACAAAGTTAT  660
Bc28.1    TGCAACAGTGGTTAACGAATTGGTGTCCCACAAAGATATGATTTACATTAACGACGCTAT  660
          ***************  *********************** *  ********  *  ***

Bc28.2    GAAAAAATATTTTGACAGGCAGAAAAAGGAGG---CTGAAAGATTGACCAAAAAGGCCGA  717
Bc28.1    GAAGCAAACGTTGATAAATGGACCAAGGAGGAGTCTGAAAGATTGGCCATGATGGCTGA  720
          ***  **  *  ****  *     **  ******    **********   *  *** **

Bc28.2    GAAGGGTATGTCTGGAGGTAAGTATAAGGTGAAAGGTTATGCAGCCCCCTCTACTTGGAT  777
Bc28.1    ACAGGGTATATCTGGAGCCAAGGGTAAGAAGGATGGATTCTCATTCGCCGGT-CTTAG-T  778
          * ****** ********  ***  ***  *  *  * ** *   ***  *  * ***  *
```

Figure 3 Cont'd.

```
                  Stop                                                Rspe3G
                                                                     ←──────
Bc28.2    GCTATGACCATGCATACAA-----GTTGCAACTAACAATTAACATTTTGAAGCCTG-TAC  831
Bc28.1    GTCATCAGCCTTCTTGTTGCCGCCGTCGCGGTTGTGGTCTAAGAGGTTAAGAATGACTAT   838
             *  ** * ** *  *          ** **    *     *** *  ** *      **
                              ←──────────                        ←──────
                                 Rspe4           Stop               Rspe3C Bc28.2    TCCTCAATGAGCTC  845
Bc28.1    TTGTGGGCGTAATG  852
          * *    *    *
```

Figure 4

```
                    ────5'UTR────▶                                                    Met
A8        AGTCGATACCTCCGAGAATAGTCTTGTATTAATCCTGTCGCTATTCACAATGAAGGGTTT 60
BcB       AGTCGATACCTCCGAGAATAGTCTTATATTAATCTTGCCGCTATTCACAATGAAGGGTTT 60
34.01     AGTCGATACCTCCGAGAATAGTCTTATATTAATCTCGCCGCTATTCACAATGAAGGGTTT 60
Castres   AGTCGATACCTCCGAGAATAGTCTTATATTAATCTTGCCGCTATTCACAATGAAGGGTTT 60
Robin     AGTCGATACCTCCGAGAATAGTCTTGTATTAATCCTGTCGCTATTCACAATGAAGGGTTT 60
BcA       AGTCGATACCTCCGAGAATAGTCTTGTATTAATCCTGTCGCTATTCACAATGAAGGGTTT 60
          ************************ *******  * ********************

Fspe3
                                                              ──────
A8        CTTCGGAATTATTTTGTCCATTATTTTTGTTCGTGCCGTTAGCTGCACTGAGGATGAGAA 120
BcB       CTTCGGAATTATTTTGTCCATTATTTTTGTTCGTGCCGTTAGCTGCACTGAGGATGAGAA 120
34.01     CTTCGGAATTATTTTGTCCATTATTTTTGTTCGTGCCGTTAGCTGCACTGAGGATGAGAA 120
Castres   CTTCGGAATTATTTTGTCCATTATTTTTGTTCGTGCCGTTAGCTGCACTGAGGATGAGAA 120
Robin     CTTCGGAATTATTTTGTCCATTATTTTTGTTCGTGCCGTTAGCTGCACTGAGGATGAGAA 120
BcA       CTTCGGAATTATTTTGTCCATTATTTTTGTTCGTGCCGTTAGCTGCACTGAGGATGAGAA 120
          ************************************************************

───────▶
A8        AAGGGATAGTGTCGTCGAGGGCGCTACGTCCGTTGAAGCCAGCTTAAAGGAGCAGATCGA 180
BcB       AAGGGATAGTGTCGTCGAGGGCGCTACGTCCGTTGAAGCCAGCTTAAAGGAGCAGATCGA 180
34.01     AAGGGATACTGTCGTCGAGGGCGCTACGTCCGTTGAAGCCAGCTTAAAGGAGCAGATCGA 180
Castres   AAGGGATAGTGTCGTCGAGGGCGCTACGTCCGTTGAAGCCAGCTTAAAGGAGCAGATCGA 180
Robin     AAGGGATAGTGTCGTCGAGGGCGCTACGTCCGTTGAAGCCAGCTTAAAGGAGCAGATCGA 180
BcA       AAGGGATAGTGTCGTCGAGGGCGCTACGTCCGTTGAAGCCAGCTTAAAGGAGCAGATCGA 180
          ******** ***************************************************

A8        CTGGCTCGCTGAACGTTATTCCGCTGACTTGACTAACAAAGACACTTCAAAATGGAATAC 240
BcB       CTGGCTCGCTGAACGTTATTCCGCTGACTTGACTAACAAAGACACTTCAAAATGGAATAC 240
34.01     CTGGCTCGCTGAACGTTATTCCGCTGACTTGACTAACAAAGACACTTCAAAATGGAATAC 240
Castres   CTGGCTCGCTGAACGTTATTCCGCTGACTTGACTAACAAAGACACTTCAAAATGGAATAC 240
Robin     CTGGCTCGCTGAACGTTATTCCGCTGACTTGACTAACAAAGACACTTCAAAATGGAATAC 240
BcA       CTGGCTCGCTGAACGTTATTCCGCTGACTTGACTAACAAAGACACTTCAAAATGGAATAC 240
          ************************************************************

A8        CGACGAGAAGGTGAAGGAGCTGTTGAATGAGAAGGCTGTTGGCATAGAGTCTCGCCTTCT 300
BcB       CGACGAGCAGGTGAAGGAGCTGTTGAATGAGAAGGCTGTTGGCATAGAGTCTCGCCTTCT 300
34.01     CAACGAGCAGGTGAAGGAACTGTTGAATGAGAAGGCTGTTGGCATAGAGTCTCGCCTTCT 300
Castres   CGACGAGCAGGTGAAGGAGCTGTTGAATGAGAAGGCTGTTGGCATAGAGTCTCGCCTTCT 300
Robin     CGACGAGAAGGTGAAGGAGCTGTTGAATGAGAAGGCTGTTGGCATAGAGTCTCGCCTTCT 300
BcA       CGACGAGAAGGTGAAGGAGCTGTTGAATGAGAAGGCTGTTGGCATAGAGTCTCGCCTTCT 300
          * ***** ********** *****************************************

A8        TGCCATTGCTAAGGAATTCCACAAATTGAAGTCCGTTCTGTGCACCGGCGTCAACGAAAC 360
BcB       TGCCATTGCTAAGGAATTCCACAAATTGAAGTCCGTTCTGTGCACCGGCGTCAACGAAAC 360
34.01     TGCCATTGCTAAGGAGTTCCACAAATTGAAGTCCGTTCTGTGCACCGGCGTCAACGAAAC 360
Castres   TGCCATTGCTAAGGAGTTCCACAAATTGAAGTCCGTTCTGTGCACCGGCGTCAACGAAAC 360
Robin     TGCCATTGCTAAGGAATTCCACAAATTGAAGTCCGTTCTGTGCACCGGCGTCAACGAAAC 360
BcA       TGCCATTGCTAAGGAATTCCACAAATTGAAGTCCGTTCTGTGCACCGGCGTCAACGAAAC 360
          *************** ********************************************

A8        TCCCGCTCATGTCGCTAACAGGGTGTCACCCGGAGACGCCATCTCCATGCTCTACGTGCT 420
BcB       TCCCGCTCATGTCGCTAACAGGGTGTCACCCGGAGACGCCATCTCCATGCTTTACGTGCT 420
34.01     TCCCGCTCATGTCGCTAACAGGGTGTCACCCGGAGACGCCATCTCCATGCTTTACGTGCT 420
Castres   TCCCGCTCATGTCGCTAACAGGGTGTCACCCGGAGATGCCATCTCCATGCTTTACGTGCT 420
Robin     TCCCGCTCATGTCGCTAACAGGGTGTCACCCGGAGACGCCATCTCCATGCTCTACGTGCT 420
BcA       TCCCGCTCATGTCGCTAACAGGGTGTCACCCGGAGACGCCATCTCCATGCTCTACGTGCT 420
          *********************************** *************** *******
```

Figure 4 Cont'd.

```
A8       TTCTATCACTCACAGGGAATTGTCTAGCCTTAAGAATAAGATCGATGAATGGAAGAAGGT 480
BcB      TTCTATCACTCACAGGGAATTGTCTAGCCTTAAGAATAAGATCGATGAATGGAAGAAGGT 480
34.01    TTCTATCACTCACAGGGAATTGTCTAGCCTTAAGAATAAGATCGATGAATGGAAGAAGGT 480
Castres  TTCTATCACTCACAGGGAATTGTCTAGCCTTAAGAATAAGATCGATGAATGGAAGAAGGT 480
Robin    TTCTATCACTCACAGGGAATTGTCTAGCCTTAAGAATAAGATCGATGAATGGAAGAAGGT 480
BcA      TTCTATCACTCACAGGGAATTGTCTAGCCTTAAGAATAAGATCGATGAATGGAAGAAGGT 480
         ************************************************************

A8       CAAGGCATCTGAAGATGGCACCAAAGTGATCCAAAATATCAAGGACGACAGGACTAACAC 540
BcB      CAAGGCATCTGACAATGGCACCAATGTGATCCAAAATATCAAGGACGACAGGACTAACAC 540
34.01    CAAGGCATCTGACAATGGCACCAATGTGATCCAAAATATCAAGGACGACAGGACTAACAC 540
Castres  CAAGGCATCTGAAGATGGCACCAAAGTGATCCAAAATATCAAGGACGACAGGACTAACAC 540
Robin    CAAGGCATCTGAAGATGGCACCAAAGTGATCCAAAATATCAAGGACGACAGGACTAACAC 540
BcA      CAAGGCATCTGAAGATGGCACCAAAGTGATCCAAAATATCAAGGACGACAGGACTAACAC 540
         ************ ********* *************************************
                           Cons3.1
                     ───────────────────▶
A8       CTGGTTCGTTGCCCATGGATTCAAGGTAGCTGAGCTCAACGATGTCACCCTTGAGAAACT 600
BcB      CTGGTTCGTTGCCCATGGATTCAAGGTAGCTGAGCTCAACGATGTAACCCTTGAGAAACT 600
34.01    CTGGTTCGTTGCCCATGGATTCAAGGTAGCTGAGCTCAACGATGTAACCCTTGAGAAAGT 600
Castres  CTGGTTCGTTGCCCATGGATTCAAGGTAGCTGAGCTCAACGATGTAACCCTTGAGAAACT 600
Robin    CTGGTTCGTTGCCCATGGATTCAAGGTAGCTGAGCTCAACGATGTCACCCTTGAGAAACT 600
BcA      CTGGTTCGTTGCCCATGGATTCAAGGTAGCTGAGCTCAACGATGTCACCCTTGAGAAACT 600
         ********************************************* *********** *

A8       TGCAACAGTGGTTAACGAATTGGTGTCCCACAAAGATATGATTTACATTAACGACGCTAT 660
BcB      TGCAACAGTGGTTAACGAATTGGTGTCCCACAATGATATGATCTACATTAACGACGCTAT 660
34.01    TGCAACAGTGGTTAACGAATTGGTGTCCCACAATGATATGATCTACATTAACGACGCTAT 660
Castres  TGCAACAGTGGTTAACGAATTGGTGTCCCACAATGATATGATCTACATTAACGACGCTAT 660
Robin    TGCAACAGTGGTTAACGAATTGGTGTCCCACAAAGATATGATTTACATTAACGACGCTAT 660
BcA      TGCAACAGTGGTTAACGAATTGGTGTCCCACAAAGATATGATTTACATTAACGACGCTAT 660
         ********************************* ******* ******************

A8       GAAGCAAAACGTTGATAAATGGACCAAGGAGGAGTCTGAAAGATTGGCCATGATGGCTGA 720
BcB      GAAGCAAAACGTTGATAAATGGACCAAGGAGGAGTCTGAAAGATTGGCCATGATGGCTGA 720
34.01    GAAGCAAAACGTTGATAAATGGAACAAGGAG---TCTGAAAGATTGGCCATGATGGCTGA 717
Castres  GAAGCAAAACGTTGATAAATGGAACAAGGAG---TCTGAAAGATTGGCCATGATGGCTGA 717
Robin    GAAGCAAAACGTTGATAAATGGACCAAGGAGGAGTCTGAAAGATTGGCCATGATGGCTGA 720
BcA      GAAGCAAAACGTTGATAAATGGACCAAGGAGGAGTCTGAAAGATTGGCCATGATGGCTGA 720
         ********************** *******    **************************

A8       ACAGGGTATATCTGGAGCCAAGGGTAAGAAGGATGGATTCTCATTCGCCGGTCTTAGTGT 780
BcB      ACAGGGTATATCTGGAGCAAAGGGTAAGAAGGATGGATTCTCATTCGCCGGTCTTAGTGT 780
34.01    ACAGGGTATATCTGGAGCAAAGGGTAAGAAGGATGGATTCTCATTCGCCGGTCTTAGTGT 777
Castres  ACAGGGTATATCTGGAGCAAAGGGTAAGAAGGATGGATTCTCATTCGCCGGTCTTAGTGT 777
Robin    ACAGGGTATATCTGGAGCCAAGGGTAAGAAGGATGGATTCTCATTCGCCGGTCTTAGTGT 780
BcA      ACAGGGTATATCTGGAGCCAAGGGTAAGAAGGATGGATTCTCATTCGCCGGTCTTAGTGT 780
         ****************** *****************************************
                              Rspe4          Stop            Rspe3C
                     ◀───────────────────                ◀───────
A8       CATCAGCCTTCTTGTTGCCGCCGTCGCGGTTGTGGTCTAAGAGGTTAAGGATGACTATTT 840
BcB      CATCAGCCTTCTTGTTGCCGCCGTCGCGGTTGTGCTCTAAGAGGTTAAGGATGACTATTT 840
34.01    CATCAGCCTTCTTGTTGCCGCCGTCGCGGTTGTGCTCTAAGAGGTTAAGGATGACTATTT 837
Castres  CATCAGCCTTCTTGTTGCCGCCGTCGCGGTTGTGCTCTAAGAGGTTAAGGATGACTATTT 837
Robin    CATCAGCCTTCTTGTTGCCGCCGTCGCGGTTGTGGTCTAAGAGGTTAAGGATGACTATTT 840
BcA      CATCAGCCTTCTTGTTGCCGCCGTCGCGGTTGTGGTCTAAGAGGTTAAGAATGACTATTT 840
         ********************************** ************** **********
```

Figure 4 Cont'd.

|  | Rspe3C |  |
|---|---|---|
| A8 | GTGGGCGTAATG | 852 |
| BcB | GTGGGCGTAATG | 852 |
| 34.01 | GTGGGCGTAATG | 849 |
| Castres | GTGGGCGTAATG | 849 |
| Robin | GTGGGCGTAATG | 852 |
| BcA | GTGGGCGTAATG | 852 |
|  | *********** |  |

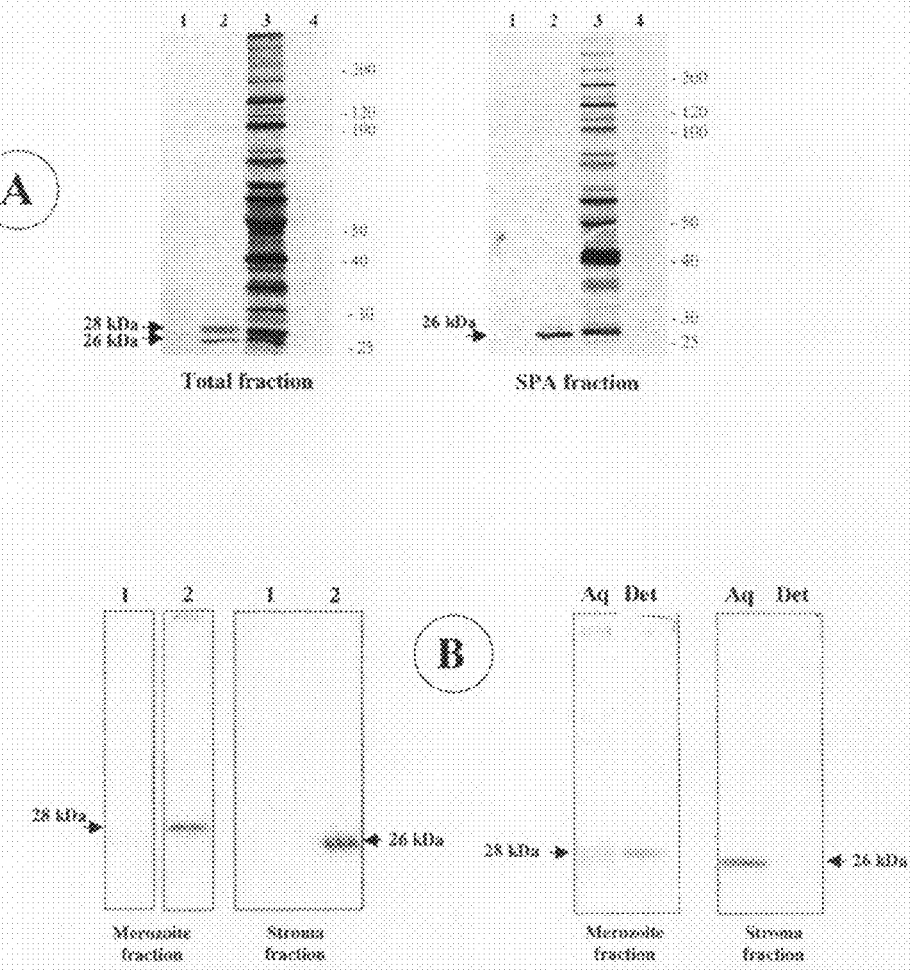

Figure 13 (continued)
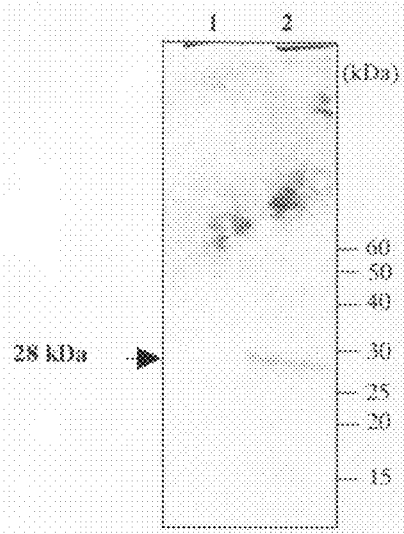
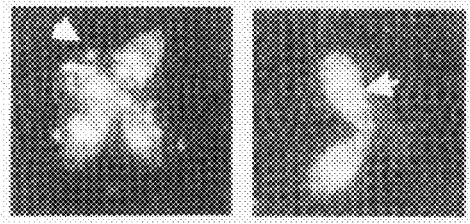

Figure 14
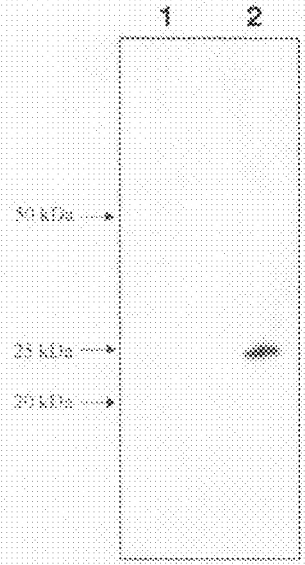
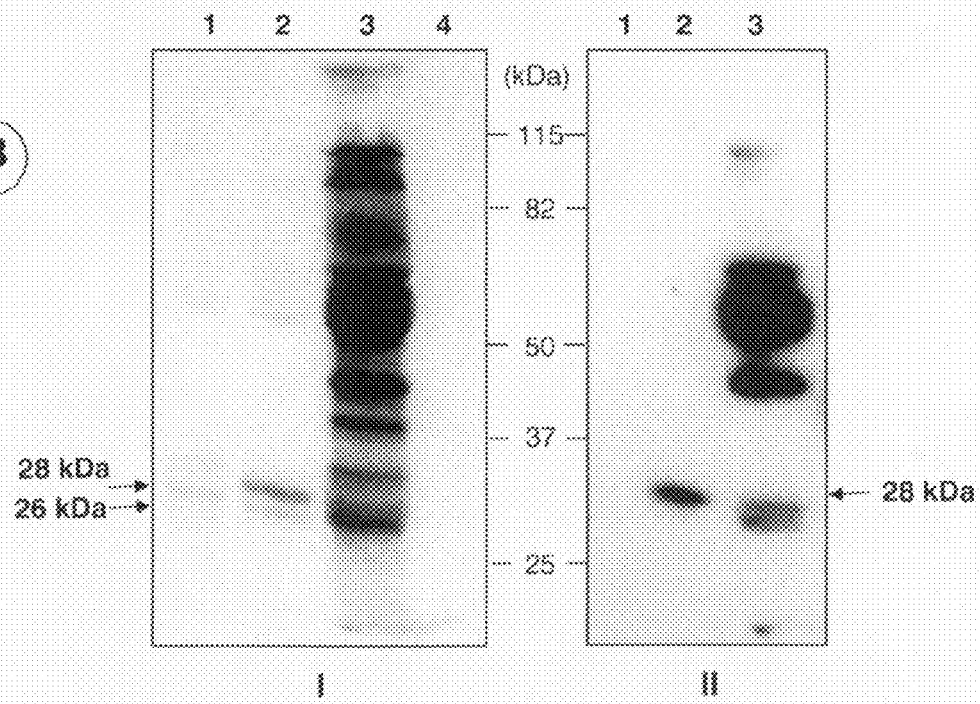

BABESIA VACCINES

The invention relates to *Babesia* proteins of a 28 kDa protein family and to immunogenic fragments thereof, to nucleic acids encoding such proteins, to cDNA fragments, recombinant DNA molecules, live recombinant carriers, and host cells, to vaccines, to methods for the preparation of such vaccines, to the use of such proteins or fragments, and to diagnostic tests.

Babesiosis, like malaria, is a disease, which has a geographically focal occurrence. The reason for this is that the pathogen is transmitted by ticks that feed on a certain reservoir of parasites present in a vertebrate population. Only where ticks are present, Babesiosis can occur. On balance, particularly in indigenous animals, the parasite coexists with the host without causing significant disease. In many cases Babesiosis becomes a problem because of man's activities through inbreeding of genetic traits and/or transporting animals to unfamiliar environments where Babesiosis is endemic (Callow, L. L. and Dalgliesh, R. J., 1982, in: "Immunology of Parasitic Infections", Cohen, S. and Warren, K. S. eds., p. 475-526, Blackwell Scientific).

Babesiosis also holds a threat as zoonotic agent, not only to immunocompromised humans (Gray et al., 2002, Int. J. Med. Microbiol., vol. 291, p. 108-111).

Signs of disease in naturally acquired Babesiosis usually begin 7-21 days after infection. These symptoms include: fever, anorexia, depression, anaemia, haemoglobinuria and rapidly developing weakness. Increased lacrimation, salivation and muscle tremor commonly occur. Nervous signs may develop in terminal infections, and death may occur when the disease is left untreated. Coagulation disturbances lead to increased erythrocyte-stickiness. Thrombosis is not common, but small hyaline thrombi, connected with megakaryocytes have been described. As a result the blood passage through the microvasculature is hampered, resulting in congestion of internal organs and decreased packed cell volumes (PCV). This might impair the oxygen supply to certain tissues and subsequently lead to tissue damage as a result of anoxia.

Species from the Babesiidae have now been detected to infect most mammalian species of veterinary importance (Kuttler, K. L., in M. Ristic ed.: "Babesiosis of domestic animals and man". CRC Press, Inc., Boca Raton, Fla., 1988): Cow (*B. divergens, B. bovis, B. bigemina*), Swine (*B. trautmanni, B. perroncitoi*), Sheep (*B. ovis, B. motasi*), Horse (*B. equi, B. caballi*), Dog (*B. canis, B. rossi, B. vogeli*), and Cat (*B. felis, B. cati*). In all these species death or more or less severe economical losses (reduction in quality or quantity of meat, milk, wool, or offspring), or severe reduction in well being are caused either as a result of the *Babesia* infection directly, or through facilitation of secondary infections.

Medications exist to cure an established *Babesia* infection, for instance dogs can be treated with imidocarb dipropionate (commercially available as Carbesia®) (Brandao et al., 2003, Vet. Paras. vol. 114, p. 253-265). However such an injection is painful due to tissue irritation. Further it suffers the common drawbacks of such anti-parasitics: the prevention of a build up of immunological memory, potential toxicity, and build up of resistance.

It has been shown that Babesiosis can be controlled by vaccination with live vaccines (Pipano, 1995, Vet. Paras., vol. 57, p. 213-231). Such vaccines are produced by harvesting erythrocytes from infected animals. For some but not all *Babesia* species in vitro erythrocyte cultures have been developed, to increase the number of parasites. The infected erythrocytes from the animal or the cultures are then used to vaccinate animals.

General disadvantages of such live parasitic vaccines are that the inoculation material is largely uncontrolled, highly variable in its composition, biologically unsafe, and on the whole the process is unethical through the use of a large number of experimental animals. Additionally, *Babesia* parasites are very unstable; as they are strictly anaerobic, they must be kept away from oxygen or will die quickly.

Alternatively, not the parasite-infected erythrocytes themselves are used for vaccination, but the surrounding serum, or culture supernatant. Such surrounding liquids of infected erythrocytes contain so-called Soluble Parasite Antigens (SPA). Little is known about the composition of these preparations. It has been suggested that the protective activity is due to the immunising capacity of antigens of the merozoite surface coat in the serum or medium, a structure that is left behind during the process of invasion of the erythrocyte (Ristic, M. and Montenegro-James, S., 1988, in: "Babesiosis of Domestic Animals and Man", Ristic, M. ed., p. 163-190, CRC Press). In addition, during in vitro culture a number of parasites die, thereby (internal) parasitic antigens are released into the culture medium.

Such SPA preparations are capable of inducing an immune response that, although not necessarily affecting the parasite, sufficiently reduces the clinical manifestations of infection (Schetters and Montenegro-James, S., 1995, Parasitology today, vol. 11, p. 456-462). For instance SPA from culture supernatant of an in vitro culture of *Babesia canis* parasite-infected erythrocytes induces protective immunity against homologous challenge infection.

An SPA vaccine for *Babesia canis* is available commercially as Pirodog®, and is prepared from the supernatant of a culture of a strain of *Babesia canis* (described in U.S. Pat. No. 4,777,036). However, such a vaccine gives in general little protection against infections with (wild type) *B. canis* (Lepetit, C., 1988, "Piroplasmose canine et vaccination Pirodog", Doctoral Thesis, Univ. of Nantes, France).

In general, SPA based vaccines bear the same disadvantages as the live parasitic vaccines do, in that they are largely uncharacterised, highly variable and require many precautions to be biologically safe. Additionally the production of such vaccines is very difficult to scale up, as that requires the infection, housing and harvesting of experimental animals to provide parasites, erythrocytes, and/or serum.

It is an object of the invention to provide proteins or fragments thereof that can serve as effective subunit vaccines for infection with Babesiidae, that are well defined, safe, stable, with easily scaleable production.

It was surprisingly found now that a subunit vaccine comprising a member of a novel *Babesia* protein family; the 28 kDa protein family, as well as immunogenic fragments thereof incorporate all these advantageous characteristics.

Many disadvantages of live parasite- and SPA vaccines can now be overcome by the use of a member of this novel protein family or of immunogenic fragments thereof in protein subunit vaccines produced in an expression system; such a protein is highly defined, biologically safe, the product can be stabilized much better than whole live parasites, and its production can be easily scaled up Proteins of the novel 28 kDa protein family are characterised in that they all share a specific amino acid sequence that is very well conserved amongst the various members of said family.

In spite of the presence of this well-conserved amino acid sequence, the overall length of the proteins of the 28 kDa protein family may well be different in the various members of the family of Babesiidae. Examples of members of the 28 kDa protein family are found to have a length ranging from below 26 kDa up to over 40 kDa.

Members of the 28 kDa protein family however all comprise a stretch of amino acids that has a level of homology of at least 70% to the amino acid sequence from amino acid position 17 to position 180 in SEQ ID NO 2.

Merely as examples, in French *Babesia canis* isolate A, members of the 28 kDa family according to the invention, and further referred to as Bc28.1 or Bc28.2, were found to have the amino acid sequence as depicted in SEQ ID NO: 2 or 4 respectively.

The proteins of the 28 kDa protein family are expressed from their respective encoding sequences that are members of a 28 kDa multigene family from Babesiidae, and have a high level of sequence identity at the nucleic acid level.

The proteins of the 28 kDa protein family can be detected in infected erythrocytes by specific antisera. These sera recognize these specific proteins of the parasite also in Western blotting and immunoprecipitation experiments. Both proteins can be expressed in an expression system. Proteins or their fragments, expressed in this way can be used to formulate a subunit vaccine, which protects mammalians from (signs of) disease upon infection with species of Babesiidae.

The Bc28.1 protein exists in two forms; a free 26 kDa SPA form, which is present in *Babesia* infected erythrocytes and in their surrounding liquid; as well as a 28 kDa bound protein form that has a GPI anchor, and is associated with the membrane of the *Babesia* merozoite and with the outer membrane of the infected erythrocyte.

Because Babesiidae parasites spend most of their live hidden inside the erythrocytes, therefore an immune-response is most effective when focussed on antigens that can be 'seen' by the immune system. The 28 kDa form of Bc28.1 is such an antigen that is presented to the exterior, which allows an immune attack specifically directed to the infected erythrocyte. The 28 kDa form of the Bc28.1 protein binds to erythrocytes. This is indicative of a role in the agglutination of erythrocytes. As this process is a major cause of pathology and the way parasites infect new erythrocytes, interference at that level also provides effective immune intervention in disease progression.

Therefore, one aspect of the invention relates to a *Babesia* protein, characterised in that said protein comprises an amino acid sequence having a homology of at least 70% with the amino acid sequence from amino acid position 17 to position 180 in SEQ ID NO 2, or an immunogenic fragment of said protein.

In a preferred embodiment, the *Babesia* protein according to the invention is characterised in that said protein comprises an amino acid sequence having a homology of at least 70% with the amino acid sequence in SEQ ID NO 2, or an immunogenic fragment of said protein.

In another preferred embodiment, the *Babesia* protein according to the invention is characterised in that said protein comprises an amino acid sequence having a homology of at least 70% with the amino acid sequence in SEQ ID NO 4, or an immunogenic fragment of said protein.

In a more preferred embodiment, the *Babesia* protein according to the invention is characterised in that it is Bc28.1 protein, preferably in the 26 kDa or in the 28 kDa form.

In an another more preferred embodiment, the *Babesia* protein according to the invention is characterised in that it is Bc28.2 protein.

The term "protein" is meant to incorporate a molecular chain of amino acids. A protein is not of a specific length and can, if required, be modified in vivo or in vitro, by, e.g. glycosylation, amidation, carboxylation or phosphorylation. Inter alia, peptides, oligopeptides and polypeptides are included within the definition. A protein or peptide can be of biologic and/or synthetic origin.

A "*Babesia* protein" according to the invention is a protein which has a counterpart in an organism of the family Babesiidae.

Preferably the organism of the family Babesiidae is an organism selected from the group consisting of the species *Babesia divergens, B. bovis, B. motasi, B. caballi, B. equi, B. canis, B. rossi, B. vogeli, B. felis, B. cati, B. ovis, B. trautmanni, B. bigemina, B. microti*, and *B. gibsoni*.

More preferably the organism of the family Babesiidae is selected from the group consisting of the species *Babesia canis, B. rossi, B. caballi, B. equi, B. bovis*, and *B. bigemina*.

An "immunogenic fragment" is understood to be a fragment of a protein of the 28 kDa protein family that still has the capability to induce antibodies directed against such 28 kDa *Babesia* proteins.

Preferably an immunogenic fragment of a protein of the 28 kDa protein family according to the invention comprises at least 8 amino acids taken from the amino acid sequence of SEQ ID NO 2 or 4. More preferably such a fragment comprises 11, 15, 20, 30, 40, 50, 100, 150, or 200 amino acids taken from the amino acid sequence of SEQ ID NO 2 or 4, in that order of preference.

Preferably, an immunogenic fragment of a protein of the 28 kDa protein family according to the invention contains an epitope of such a protein. For instance an immunogenic fragment of a protein of the 28 kDa protein family according to the invention is formed by a part of the protein that lacks the N-terminal signal sequence and/or the C-terminal GPI anchor sequence. Other fragments are for Instance those comprising a specific epitope from a protein of the 28 kDa protein family. Such epitopes may be determined by the methods outlined below. All these immunogenic fragments are embodied in the invention.

An epitope is understood to be that part of an antigenic molecule to which a T-cell receptor will respond, or to which B-cells will produce antibodies. An epitope according to the invention will therefore induce specific T-cells or activate B-cells to produce specific antibodies such that these cells or antibodies give rise to an immune reaction that interferes with the course of an infection or disease. Thus, through such epitopes, an immune response can be generated.

In order to be antigenic, an amino acid fragments need to be of a certain length. Therefore an epitope consists of at least 8-11 amino acids for MHC I receptor binding, or of at least 11-15 amino acids for MHC II receptor binding (reviewed e.g. by R. N. Germain & D. H. Margulies, 1993, Annu. Rev. Immunol., vol. 11, p. 403-450, in: "The biochemistry and cell biology of antigen processing and presentation"). Amino acid fragments shorter than this may not be antigenic as such: they need to be coupled to a carrier, such as KLH, BSA or the like, using techniques known in the art. When coupled such short fragments may well be able to induce an immune response that is within the object of the invention.

Identification of immunogenic fragments or epitopes of a protein of the 28 kDa protein family according to the invention, can be easily performed by a variety of straightforward techniques, for instance by the so-called PEPSCAN method, or via computer algorithms that make comparisons to known epitopes.

The PEPSCAN method (WO 84/03564, and WO 86/06487, and H. Geysen et al., Proc. Natl. Acad. Sci. USA, 1984, vol. 81, p. 3998-4002, and J. of Immunol. meth., 1987, vol. 102, p. 259-274), is an easy to perform, quick and well-established method for the detection of immunologic determinants of a protein. It comprises the synthesis of a series of peptide fragments progressively overlapping the protein under study, and subsequent testing of these polypeptides with specific antibodies to the protein. Such antibodies to the proteins according to the invention can be obtained by making polyclonal or monoclonal antibodies, by using techniques well known in the art.

The use of computer algorithms in the designation of specific protein fragments as the immunologically important epitopes on the basis of their sequential and/or structural agreement with epitopes that are known, is also a well known technique. The determination of these regions can be based on a combination of the hydrophilicity criteria according to Hopp and Woods (1981, Proc. Natl. Acad. Sci. USA, vol. 78, p. 3824-3828), and the secondary structure aspects according to Chou and Fasman (1987, Advances in Enzymology, vol. 47, p. 45-148, and U.S. Pat. No. 4,554,101). Immunogenic epitopes can likewise be predicted from the protein's amino acid sequence by computer with the aid of Berzofsky's amphiphilicity criterion (1987, Science, vol. 235, p. 1059-1062 and U.S. patent application Ser. No. NTIS 07/005,885). A condensed overview of the use of these methods is found in Shan Lu (common principles; 1991, Tibtech, vol. 9, p. 238-242), Good et al. (Malaria epitopes; 1987, Science, vol. 235, p. 1059-1062), Lu (review; 1992, Vaccine, vol. 10, p. 3-7), and Berzofsky (HIV-epitopes; 1991, The FASEB Journal, vol. 5, p. 2412-2418).

An illustration of the effectiveness of using these methods was published by H. Margalit et al. (1987, J. of Immunol., vol. 138, p. 2213-2229) who describe success rates of 75% in the prediction of T-cell epitopes using such methods.

The percentage of homology between the proteins according to the invention is determined with the computer program "BLAST 2 SEQUENCES" by selecting sub-program: "BlastP" (T. Tatusova & T. Madden, 1999, FEMS Microbiol. Letters, vol. 174, p. 247-250), that can be found at www.ncbi.nlm.nih.gov/blast/bl2seq/bl2.html. The comparison-matrix that is used is: "blosum62", with the default parameters: open gap penalty: 11; extension gap penalty: 1, and gap x_dropoff: 50.

This program lists the percentage of amino acids that are identical as "Identities", and the percentage of amino acids that are homologous as "Positives"

For example, the amino acid sequences of Bc28.1 and Bc28.2 are aligned in FIG. 1. A high percentage of homology exists between the two proteins, especially in the N-terminal 3/4$^{rs}$. The percentage homologies (the percentage of "positives" from the BlastP program) are presented in Table 1.

TABLE 1

Results of BlastP amino acid alignment of Bc28.1 and Bc2B.2 proteins.

|  | Amino acids | Percentage homology |
|---|---|---|
| Complete | 244 | 91 |
| N-terminal | 180 | 97 |
| C-terminal | 64 | 73 |

It will be understood that, for a particular protein of the 28 kDa protein family, natural variations exist between the proteins associated with individual strains or species of Babesiidae. These variations may be demonstrated by (an) amino acid difference(s) in the overall sequence or by deletions, substitutions, insertions, inversions or additions of (an) amino acid(s) in said sequence. Amino acid substitutions, which do not essentially alter biological and immunological activities, have been described, e.g. by Neurath et al., 1979, in: "The Proteins", Academic Press New York. Amino acid replacements between related amino acids or replacements which have occurred frequently in evolution are, i.a. Ser/Ala, Ser/Gly, Asp/Gly, Asp/Asn, Ile/Val (see Dayhof, M. D., 1978, "Atlas of protein sequence and structure", Nat Biomed. Res. Found., Washington D.C. vol. 5, suppl. 3). Other common amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (1985, Science, vol. 227, p. 1435-1441) and determining the functional similarity between homologous proteins. Such amino acid substitutions of the exemplary embodiments of this invention, as well as variations having deletions and/or insertions are within the scope of the invention as long as the resulting proteins retain immune reactivity. Those variations in the amino acid sequence of a certain protein according to the invention that still provide a protein capable of inducing an immunological response against an organism of the family Babesiidae are considered as "not essentially influencing the immunogenicity", and are an embodiment of the invention.

This explains why proteins of the 28 kDa protein family according to the invention, when isolated from different species, may have homology percentages of 70 or more to the amino acid sequences in SEQ ID NO: 2 or 4, while still representing the same protein with the same immunological characteristics, i.e. the capability of inducing an immunological response against an organism of the family Babesiidae.

Proteins of the 28 kDa protein family according to the invention can be obtained from member species of the Babesiidae family.

However in an even more preferred embodiment, the proteins of the 28 kDa protein family according to the invention or immunogenic fragments thereof are characterised in that they are obtained from *B. divergens, B. bovis, B. motasi, B. caballi, B. equi, B. canis, B. rossi, B. vogeli, B. felis, B. cati, B. ovis, B. trautmanni, B. bigemina, B. microti,* or *B. gibsoni*.

Still even more preferably the proteins of the 28 kDa protein family according to the invention or immunogenic fragments thereof are characterised in that they are obtained from *Babesia canis, B. rossi, B. caballi, B. equi, B. bovis,* or *B. bigemina*.

With respect to the current taxonomic classification, the skilled person will realise this may change over time, as new insights lead to reclassification into new groups or to addition to existing groups. However, as this does not change the protein repertoire of the organism involved, only its classification, such re-classified organisms are considered to be embodied by the invention. For example *B. canis* and *B. rossi* were formerly classified as subspecies *B. canis canis* and *B. canis rossi*.

Sibinovic K., et al. (1967, J. of Paras., vol. 53, p. 919-923) studied isolated *Babesia* antigens from serum of horses infected with *Babesia equi* and *B. caballi*, and from dogs infected with *B. canis*. Significant similarities were noted in the biochemical characteristics of the antigens from these species. The *Babesia* proteins of the 28 kDa protein family according to the invention as obtained from *B. canis* will therefore also be present in *B. equi* and *B. caballi*, and in other species of the Babesiidae family.

Figure 11:
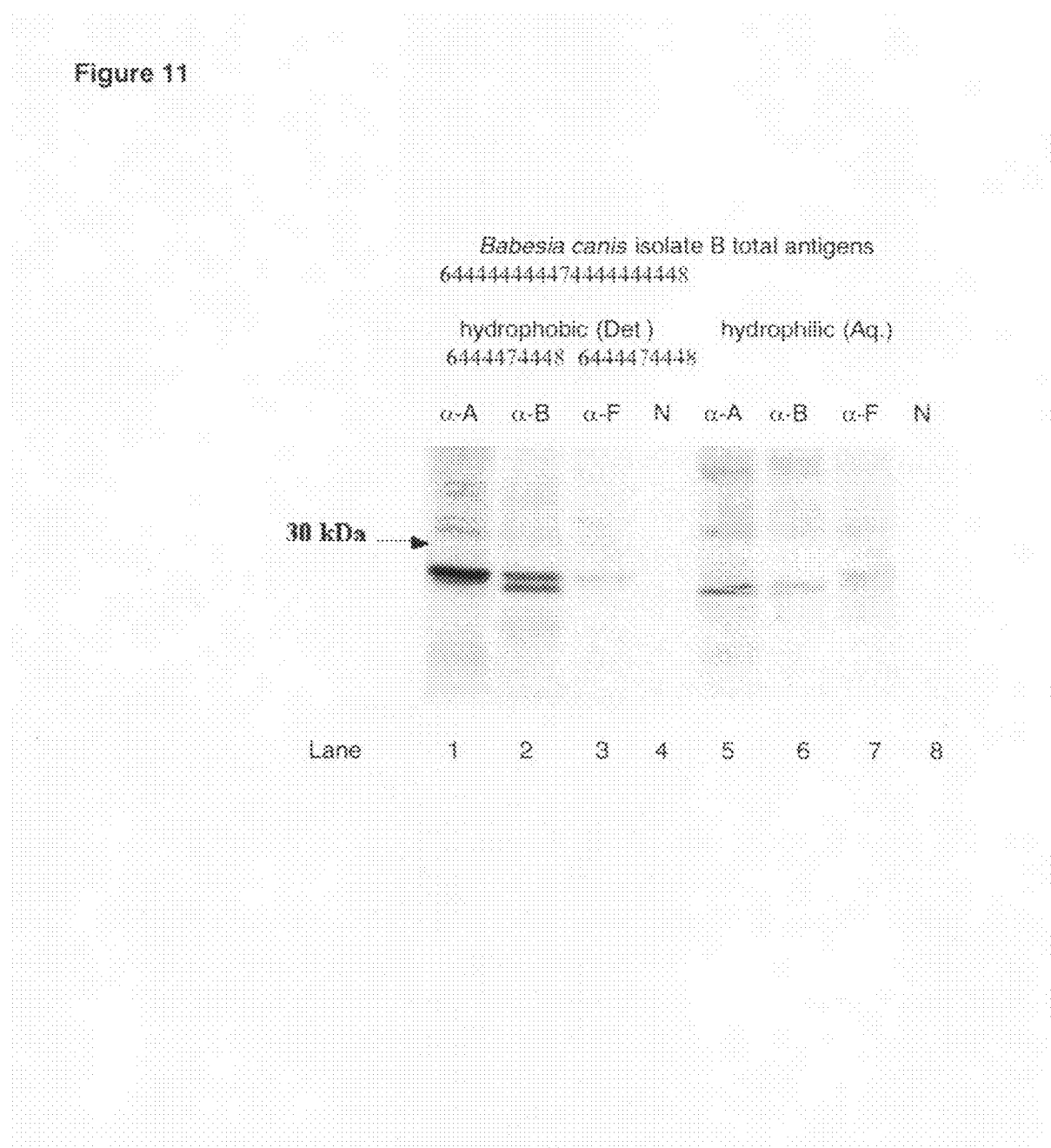

In Example II, section 2.2.5. and FIG. 11 the specific recognition of the 26 and 28 kDa forms of Bc28.1 protein from *B. canis* by an antiserum against *B. rossi* is disclosed.

This illustrates proteins of the 28 kDa protein family present in B. rossi are immunologically related to those in B. canis.

Bc28.1 coding sequences have been obtained from geographically and genetically disparate B. canis field isolates. The deduced amino acids of a few examples of such isolates are aligned in FIG. 2. The percentage homologies ("Positives") determined by pairwise alignment using the BlastP program are presented in Table 2.

TABLE 2

Percentage homologies of pair-wise BlastP amino acid alignments between the complete Bc28.1 proteins from geographically and genetically disparate B. canis field isolates. Bc28.1 proteins were 255 or 256 amino acids long.

|         | Robin | A8  | B   | 34.01 |
|---------|-------|-----|-----|-------|
| A8      | 100   |     |     |       |
| B       | 98    | 98  |     |       |
| 34.01   | 97    | 97  | 98  |       |
| Castres | 98    | 98  | 97  | 99    |

Therefore, in the most preferred embodiment the invention relates to a Bc28.1 or a Bc28.2 protein or an immunogenic fragment of said proteins, characterised in that said proteins or immunogenic fragments are obtained from a B. canis isolate selected from the group consisting of A8, B, 34.01, A, Robin, and Castres.

A protein named Bd37, from Babesia divergens has been described before (EP 1050541 A1). At first instance Bd37 may appear to resemble the proteins Bc28.1 and Bc28.2. However, Bd37 and the two Bc28 proteins are totally unrelated:

- there is no significant sequence similarity between Bd37 protein or its coding sequence, and either of the two Bc28 proteins or their coding sequences.
- an antiserum against Bd37 does not recognize the 26/28 and 45 kDa proteins of B. canis that are recognized by antibodies against Bc28.1 and 28.2 respectively, neither in Western blot nor in immunoprecipitation experiments; for instance an antiserum against Bd37-His protein does not recognize a GST-Bc28.2 protein (FIG. 10, B, lane 6).
- whereas both Bd37 and Bc28.1 are attached to the erythrocyte's outer membrane, Bd37 can be eluted off with 0.5 M NaCl, while Bc28.1 remains associated even at elution with 2 M NaCl (Example II, sections 2.1.5.1. and 2.2.6.1.)

The preferred way to produce the proteins of the 28 kDa protein family according to the invention is by using genetic engineering techniques and recombinant expression systems. These may comprise using nucleic acids, cDNA fragments, recombinant DNA molecules, live recombinant carriers, and/or host cells.

Therefore, another aspect of the invention relates to a nucleic acid, characterised in that it encodes the proteins of the 28 kDa protein family according to the invention, or an immunogenic fragment of said protein.

In a preferred embodiment the nucleic acid according to the invention comprises the nucleic acid of SEQ ID NO: 1.

In another preferred embodiment the nucleic acid according to the invention comprises the nucleic acid of SEQ ID NO: 3.

The term "nucleic acid" is meant to incorporate a molecular chain of desoxy- or ribonucleic acids. A nucleic acid is not of a specific length, therefore polynucleotides, genes, open reading frames (ORF's), probes, primers, linkers, spacers and adaptors are included within the definition. A nucleic acid can be of biologic and/or synthetic origin. The nucleic acid may be in single stranded or double stranded form. The single strand may be in sense or anti-sense orientation. Also included within the definition are modified RNAs or DNAs. Modifications in the bases of the nucleic acid may be made, and bases such as Inosine may be incorporated. Other modifications may involve, for example, modifications of the backbone.

The term "encodes" is meant to incorporate providing the possibility of protein expression, i.a. through transcription and/or translation when brought into the right context.

A nucleic acid according to the invention encodes a protein of the 28 kDa protein family according to the invention, or encodes an immunogenic fragment of said protein.

A nucleic acid according to the invention has a minimal length of 24 nucleotides taken from the nucleic acid sequence of SEQ ID NO 1 or 3, preferably a nucleic acid according to the invention comprises 50, 100, 250, or 500 nucleotides taken from the nucleic acid sequence of SEQ ID NO 1 or 3, in that order of preference.

A nucleic acid according to the invention for instance is a nucleic acid encoding a protein of the 28 kDa protein family according to the invention without a signal sequence and/or a GPI anchor. Other nucleic acids may comprise a sequence encoding a specific epitope of a protein of the 28 kDa protein family. Such nucleic acids are all embodied in the invention.

The percentage of identity between nucleic acids according to the invention is determined with the computer program "BLAST 2 SEQUENCES" by selecting sub-program: "BlastN" (T. Tatusova & T. Madden, 1999, FEMS Microbiol. Letters, vol. 174, p. 247-250), that can be found at www.ncbi.nlm.nih.gov/blast/bl2seq/bl2.html. Parameters that are used are the default parameters: reward for a match: +1; penalty for a mismatch: −2; open gap penalty: 5; extension gap penalty: 2; and gap x_dropoff: 50. Unlike the output of the BlastP program described above, the BlastN program does not list homologies, but identities; the percentage of nucleotides that are identical are indicated as "Identities".

It is well known in the art, that many different nucleic acids can encode one and the same protein. This is a result of what is known in molecular biology as "wobble", or the "degeneracy of the genetic code"; when several codons or triplets of mRNA will cause the same amino acid to be attached to the chain of amino acids growing in the ribosome during translation. It is most prevalent in the second and especially the third base of each triplet encoding an amino acid. This phenomenon can result in a heterology of about 30% for two different nucleic acids that still encode the same protein. Therefore, two nucleic acids having a nucleotide sequence identity of about 70% can still encode one and the same protein.

For example, the nucleic acids encoding the Bc28.1 and Bc28.2 proteins according to the invention are aligned in FIG. 3. A high percentage of identity exists between the two coding sequences, especially in the 5' 3/4$^{rs}$ of the coding sequence. The percentage identities from the BlastN program are presented in Table 3.

TABLE 3

| Results of BlastN nucleotide sequence alignments between the nucleic acids encoding the Bc28.1 and Bc28.2 proteins according to the invention. | | |
|---|---|---|
| | Nucleotides | Percentage identity |
| Complete | 845 | 94 |
| 5' | 652 | 97 |
| 3' | 193 | 81 |

Nucleic acids encoding the proteins of the 28 kDa protein family according to the invention can be obtained from member species of the Babesiidae family.

However in a more preferred embodiment, the nucleic acids encoding a protein of the 28 kDa protein family or immunogenic fragments thereof according to the invention are characterised in that they are obtained from *B. divergens, B. bovis, B. motasi, B. caballi, B. equi, B. canis, B. rossi, B. vogeli, B. felis, B. cati, B. ovis, B. trautmanni, B. bigemina, B. microti*, or *B. gibsoni*.

In an even more preferred embodiment the nucleic acids encoding a protein according to the 28 kDa protein family or immunogenic fragments thereof are characterised in that they are obtained from *Babesia canis, B. rossi, B. caballi, B. equi, B. bovis*, or *B. bigemina*.

The possibility of species being taxonomically re-classified has been discussed above. As this does not change the organism's genome, such reclassified organisms are also embodied in the invention.

Also embodied in the invention are proteins of the 28 kDa protein family and nucleic acids encoding them from non-mammalian Babesiidae; such proteins or genes are present due to the high conservation of the proteins of the 28 kDa protein family, their encoding sequences, their genes, and gene-family.

Nucleic acids encoding Bc28.1 protein have been obtained from geographically and genetically disparate *B. canis* field isolates. The nucleotide sequences of a few examples of such isolates are aligned in FIG. 4. The percentage identities of pairwise BlastN alignments are presented in Table 4.

TABLE 4

| Percentage identities of pair-wise BlastN nucleotide sequence alignments between the nucleic acids encoding Bc28.1 proteins from geographically and genetically disparate *B. canis* field isolates. These nucleic acids were 849 or 852 nucleotides long. | | | | |
|---|---|---|---|---|
| | Robin | A8 | B | 34.01 |
| A8 | 100 | | | |
| B | 98 | 98 | | |
| 34.01 | 97 | 97 | 98 | |
| Castres | 98 | 98 | 98 | 98 |

Nucleic acids encoding the proteins of the 28 kDa protein family according to the invention can be obtained, manipulated and expressed by standard molecular biology techniques that are well-known to the skilled artisan, and are explained in great detail in standard text-books like Sambrook & Russell: "Molecular cloning: a laboratory manual" (2001, Cold Spring Harbour Laboratory Press; ISBN: 0879695773). One such type of manipulations is the synthesis of a cDNA fragment from RNA, preferably from mRNA which can be isolated from parasites, or parasite-infected cells or -organisms by techniques known in the art.

Therefore, in another preferred embodiment, the invention relates to a cDNA fragment according to the invention.

The preferred method of obtaining a cDNA fragment by reverse transcription is through a polymerase chain reaction (PCR) technique. Standard techniques and protocols for performing PCR are for instance extensively described in C. Dieffenbach & G. Dveksler: "PCR primers: a laboratory manual" (1995, CSHL Press, ISBN 879694473).

In still another preferred embodiment, the invention relates to a recombinant DNA molecule comprising a nucleic acid according to the invention, or a cDNA fragment according to the invention, under the control of a functionally linked promoter.

To construct a recombinant DNA molecule according to the invention, preferably DNA plasmids are employed. Such plasmids are useful e.g. for enhancing the amount of DNA-insert, as a probe, and as tool for further manipulations. Examples of such plasmids for cloning are plasmids of the pBR, pUC, and pGEM series; all these are available from several commercial suppliers.

The nucleic acid encoding a protein of the 28 kDa protein family according to the invention or an immunogenic fragment of said protein, can be cloned into separate plasmids and be modified to obtain the desired conformation using techniques well known in the art. However they may also be combined into one construct for improved cloning or expression purposes.

Modifications to the coding sequences encoding a protein of the 28 kDa protein family according to the invention may be performed e.g. by using restriction enzyme digestion, by site directed mutations, or by polymerase chain reaction (PCR) techniques.

For the purpose of protein purification or -detection, or improvement of expression level, additional nucleic acids may be added. This may result in the final nucleic acid comprised in the cDNA fragment, or in the recombinant DNA molecule being larger than the sequences required for encoding a protein of the 28 kDa protein family. When such additional elements are inserted in frame, these become an integral part of the protein of the 28 kDa protein family that is expressed. Such fused proteins are also embodied in the invention An essential requirement for the expression of a nucleic acid, cDNA fragment, or recombinant DNA molecule is that these are operably linked to a transcriptional regulatory sequence such that this is capable of controlling the transcription of the nucleic acid, cDNA, or recombinant DNA. Transcriptional regulatory sequences are well known in the art and comprise i.a. promoters and enhancers. It is obvious to those skilled in the art that the choice of a promoter extends to any eukaryotic, prokaryotic or viral promoter capable of directing gene transcription, provided that the promoter is functional in the expression system used.

In yet another preferred embodiment, the invention relates to a live recombinant carrier comprising a nucleic acid according to the invention, a cDNA fragment according to the invention, or a recombinant DNA molecule according to the invention.

Such live recombinant carriers (LRC's) are e.g. micro-organisms such as bacteria, parasites and viruses in which additional genetic information has been cloned, in this case a nucleic acid, a cDNA, or a recombinant DNA molecule, encoding a protein of the 28 kDa protein family according to the invention or an immunogenic fragment thereof. Target mammalians inoculated with such LRCs will produce an immunogenic response not only against the immunogens of the carrier, but also against the heterologous protein(s) or immunogenic fragment(s) for which the genetic code is additionally cloned into the LRC, e.g. a sequence encoding a protein of the 28 kDa protein family, or an immunogenic fragment thereof.

As an example of bacterial LRCs, attenuated *Salmonella* strains known in the art can attractively be used.

Alternatively, live recombinant carrier parasites have i.a. been described by Vermeulen, A. N. (1998, Int. Journ. Parasitol., vol. 28, p. 1121-1130).

LRC viruses may be used as a way of transporting a nucleic acid into a target cell. Live recombinant carrier viruses are also called vector viruses. Viruses often used as vectors are Vaccinia viruses (Panicali et al., 1982, Proc. Natl. Acad. Sci. USA, vol. 79, p. 4927), Herpesviruses (EP 047321-A2), and Retroviruses (Valerio, D. et al., 1989, in: Baum, S. J., Dicke, K. A., Lotzova, E. and Pluznik, D. H. (Eds.), "Experimental Haematology today", Springer Verlag, New York: pp. 92-99).

The technique of in vivo homologous recombination, well known in the art, can be used to introduce a recombinant nucleic acid according to the invention into the genome of an LRC bacterium, parasite or virus of choice, capable of inducing expression of the inserted nucleic acid, cDNA or recombinant DNA according to the invention in the host animal.

Bacterial, yeast, fungal, insect, and vertebrate cell expression systems are used as host cells for expression purposes very frequently. Such expression systems are well known in the art and generally available, e.g. commercially through Invitrogen (the Netherlands).

Therefore, in yet still another preferred embodiment, the invention relates to a host cell comprising a nucleic acid according to the invention, a cDNA fragment according to the invention, a recombinant DNA molecule according to the invention, or a live recombinant carrier according to the invention.

A host cell to be used for expression of a protein of the 28 kDa protein family according to the invention may be a cell of bacterial origin, e.g. from *Escherichia coli, Bacillus subtilis, Lactobacillus* sp. or *Caulobacter crescentus*, in combination with the use of bacteria-derived plasmids or bacteriophages for expressing the sequence encoding the Bc28 protein. The host cell may also be of eukaryotic origin, e.g. yeast-cells in combination with yeast-specific vector molecules, or higher eukaryotic cells, like insect cells (Luckow et al, 1988, Biotechnology, vol. 6, p. 47-55) in combination with vectors or recombinant baculoviruses; plant cells in combination with e.g. Ti-plasmid based vectors or plant viral vectors (Barton, K. A et al., 1983, Cell, vol. 32, p. 1033); or mammalian cells like Hela cells, Chinese Hamster Ovary cells or Crandell-Rees feline kidney-cells, also with appropriate vectors or recombinant viruses.

Next to these expression systems, plant cell, or parasite-based expression systems are attractive expression systems. Parasite expression systems are e.g. described in the French Patent Application, publication number 2 714 074, and in U.S. NTIS publication U.S. Ser. No. 08/043,109 (Hoffman, S. & Rogers, W., 1993). Plant cell expression systems for polypeptides for biological application are e.g. discussed in R. Fischer et al. (1999, Eur. J. of Biochem., vol. 262, p. 810-816), and J. Larrick et al. (2001, Biomol. Engin., vol. 18, p. 87-94).

Expression may also be performed in so-called cell-free expression systems. Such systems comprise all essential factors for expression of an appropriate recombinant nucleic acid, operably linked to a promoter that will function in that particular system. Examples are the *E. coli* lysate system (Roche, Basel, Switzerland), or the rabbit reticulocyte lysate system (Promega corp., Madison, USA).

The protein of the 28 kDa protein family according to the invention or immunogenic fragments of said protein is very well suited for the production of a protein subunit vaccine. Such proteins or fragments can be obtained from parasites, or from animals or cells infected with Babesiidae parasites. However, much more convenient is the use of the nucleic acids encoding the protein of the 28 kDa protein family according to the invention or an immunogenic fragment of said protein, in an expression system. This is followed by harvesting the proteins or fragments produced and formulating these into a protein subunit vaccine, e.g. by admixing a protein of the 28 kDa protein family according to the invention or an immunogenic fragment of said protein, and a pharmaceutically acceptable carrier.

Therefore, yet another aspect of the invention relates to a vaccine comprising a protein according to the invention or an immunogenic fragment of said protein, a nucleic acid, a cDNA fragment, a recombinant DNA molecule, a live recombinant carrier, or a host cell according to the invention, or a combination thereof, and a pharmaceutically acceptable carrier.

As described above, a protein of the 28 kDa protein family or an immunogenic fragment of said protein can advantageously be used for vaccination. If such proteins or fragments do not produce an immune response on their own, they can be coupled to a carrier such as KLH, BSA or the like.

The coupling of protein or fragments thereof can also be done to enhance or modify the immune response induced. For instance it is common practice to couple protein(-fragment)s to Tetanus toxoid to enhance the response of T-cells. Also specific effector molecules may be added, such as a toxin, to improve the killing of target cells. Such couplings can be performed

- chemically, by coupling, conjugation or cross-linking, through dehydration, esterification, etc, of the amino acid sequences either directly or through an intermediate structure.
- physically, by coupling through capture in or on a macromolecular structure, or preferably
- by molecular biological fusion, through the combination of recombinant nucleic acid molecules which comprise fragments of nucleic acid capable of encoding each of the two, such that a single continuous expression product is finally produced. Molecular engineering techniques are preferred.

An alternative and efficient way of vaccination is by direct vaccination with DNA encoding the relevant antigen or epitope. Direct vaccination with DNA encoding proteins has been successful for many different proteins, as reviewed in e.g. Donnelly et al. (1993, The Immunologist, vol. 2, p. 20-26). For example in the field of anti-parasite vaccines, protection against e.g. *Plasmodium yoelii* has been obtained with DNA-vaccination with the *P. yoelii* circumsporozoite gene (Hoffman, S. et al., 1994, Vaccine, vol. 12, p. 1529-1533), and protection against *Leishmania major* has been obtained with DNA-vaccination with the *L. major* surface glycoprotein gp63 gene (Xu & Liew, 1994, Vaccine, vol. 12, p. 1534-1536).

Such a DNA vaccination can be performed with a nucleic acid, a cDNA fragment, or preferably with a recombinant DNA molecule according to the invention.

Therefore, one preferred embodiment relates to a vaccine according to the invention, characterised in that it comprises a nucleic acid, a cDNA fragment, or a recombinant DNA molecule according to the invention.

Alternatively, a vaccine according to the invention can comprise live recombinant carriers as described above, capable of expressing the protein of the 28 kDa protein family according to the invention or immunogenic fragments of said protein. Such vaccines, e.g. based upon a bacterial, a parasitic or a viral carrier or vector have the advantage over subunit vaccines that they better mimic the natural way of infection by Babesiidae. Also the presentation of the antigens by cells infected with the carriers resembles the route proteins of the 28 kDa protein family or their immunogenic fragments are presented to the immune system in a natural infection. Moreover, their self-propagation is an advantage since only low amounts of the recombinant carrier are necessary for immunisation.

Thus, another preferred embodiment relates to a vaccine according to the invention, which comprises a live recombinant carrier and a pharmaceutically acceptable carrier.

The host cells as described above can be used to express a protein of the 28 kDa protein family according to the invention or an immunogenic fragment of said protein as an expression system. After expression the proteinacious product may be harvested, but alternatively the culture medium or the complete host cells themselves may be used in a vaccine. This has the benefit of omitting purification steps, but of course requires some tolerance by the target mammalians for the media components and/or components of the host cells.

Also embodied in the invention is a vaccine according to the invention devised of a combination from two or more types of molecules from the protein or immunogenic fragment thereof, nucleic acid, cDNA, recombinant molecule, live recombinant carrier, and host cells according to the invention. These may be combined in a single dose or in separate doses, and may be given at the same time or sequentially. For instance, a combination vaccination of an initial priming with a recombinant DNA plasmid carrying the coding sequence of a protein of the 28 kDa protein family, followed some time later by a booster vaccination with a protein of the 28 kDa protein family may advantageously be used.

Vaccines according to the invention, can be administered in amounts containing between 0.1 and 1000 µg of a protein of the 28 kDa protein family according to the invention or an immunogenic fragment of said protein per mammalian target. Smaller or larger doses can in principle be used; preferably a dose of between 50 and 200 µg of a protein of the 28 kDa protein family or an immunogenic fragment thereof is used.

For live viral vector vaccines the dose rate per animal may range from 1 to $10^{10}$ pfu, preferably $10\text{-}10^5$ pfu are used.

A pharmaceutically acceptable carrier is understood to be a compound that does not adversely effect the health of the animal to be vaccinated, at least not to the extend that the adverse effect is worse than the effects seen when the animal is not vaccinated. A pharmaceutically acceptable carrier can be e.g. sterile water or a sterile physiological salt solution. In a more complex form the carrier can e.g. be a buffer.

Often, a vaccine is mixed with stabilizers, e.g. to protect degradation-prone components from being degraded, to enhance the shelf-life of the vaccine, or to improve freeze-drying efficiency. Useful stabilizers are i.a. SPGA (Bovarnik et al., 1950, J. Bacteriology, vol. 59, p. 509), skimmed milk, gelatins, bovine serum albumin, carbohydrates e.g. sorbitol, mannitol, trehalose, starch, sucrose, dextran or glucose, proteins such as albumin or casein or degradation products thereof, and buffers, such as alkali metal phosphates.

The vaccine according to the invention may additionally comprise a so-called "vehicle". A vehicle is a compound to which the proteins, protein fragments, nucleic acids or parts thereof, cDNA's, recombinant molecules, live recombinant carriers, and/or host cells according to the invention adhere, without being covalently bound to it. Such vehicles are i.a. bio-microcapsules, micro-alginates, liposomes, macrosols, aluminium-hydroxide, -phosphate, -sulphate or -oxide, silica, Kaolin®, and Bentonite®, all known in the art.

An example is a vehicle in which the antigen is partially embedded in an immune-stimulating complex, the so-called ISCOM® (EP 109.942, EP 180.564, EP 242.380).

In addition, the vaccine according to the invention may comprise one or more suitable surface-active compounds or emulsifiers, e.g. Span® or Tween®.

For reasons of e.g. stability or economy the proteins, immunogenic fragments thereof, nucleic acids, cDNA's, recombinant molecules, live recombinant carriers, host cells and vaccines according to the invention may be freeze-dried. In general this will enable prolonged storage at temperatures above zero ° C., e.g. at 4° C.

Procedures for freeze-drying are known to persons skilled in the art; equipment for freeze-drying at different scales is available commercially.

Therefore, in a more preferred embodiment, the vaccine according to the invention is characterised in that it is in a freeze-dried form.

To reconstitute the freeze-dried vaccine, it may be suspended in a physiologically acceptable diluent. Such a diluent can e.g. be as simple as sterile water, or a physiological salt solution. In a more complex form it may be suspended in an emulsion as outlined in PCT/EP99/10178.

Target subjects for the vaccine according to the invention are preferably mammalian, e.g. humans or mammalian animals of veterinary importance. The target may be healthy or diseased, and may be seropositive or -negative for Babesiidae parasites or for antibodies to Babesiidae parasites. The target subject can be of any age at which it is susceptible to the vaccination and/or to the infection or clinical disease the vaccination aims to protect against.

The more preferred target mammalians for the vaccine according to the invention are cows, horses, dogs and cats.

The vaccine according to the invention can equally be used as prophylactic and as therapeutic treatment, and interferes with the establishment and/or with the progression of an infection or its clinical symptoms of disease.

The vaccine according to the invention can be in several forms, e.g.: a liquid, a gel, an ointment, a powder, a tablet, or a capsule, depending on the desired method of application to the target.

Preferably the vaccine is in the form of an injectable liquid.

The vaccine according to the invention can be administered to the mammalian target according to methods known in the art. For instance by parenteral applications such as through all routes of injection into or through the skin: e.g. intramuscular, intravenous, intraperitoneal, intradermal, submucosal, or subcutaneous. Alternative routes of application that are feasible are by topical application as a drop, spray, gel or ointment to the mucosal epithelium of the eye, nose, mouth, anus, or vagina, or onto the epidermis of the outer skin at any part of the body; by spray as aerosol, or powder. Alternatively, application can be via the alimentary route, by combining with the food, feed or drinking water e.g. as a powder, a liquid, or tablet, or by administration directly into the mouth as a liquid, a gel, a tablet, or a capsule, or to the anus as a suppository.

The preferred application route is by intramuscular or by subcutaneous injection.

It goes without saying that the optimal route of application will depend on the particularities of the parasitic infection or clinical disease that is to be prevented or ameliorated, and the characteristics of the vaccine formulation that is used.

The scheme of the application of the vaccine according to the invention to the target mammalian can be in single or multiple doses, which may be given at the same time or sequentially, in a manner compatible with the dosage and formulation, and in such an amount as will be immunologically effective.

Preferably the vaccine is applied in one single dose that will provide sufficient immunological protection for at least a year.

In an even more preferred embodiment, the vaccine according to the invention is characterised in that it comprises an adjuvant.

An adjuvant in general is a substance that boosts the immune response of the target in a non-specific manner. Many different adjuvants are known in the art. Examples of adjuvants are Freund's Complete and -Incomplete adjuvant, vitamin E, non-ionic block polymers and polyamines such as dextransulphate, carbopol and pyran. Also very suitable are saponins, which are the preferred adjuvant. Saponins are preferably added to the vaccine at a level between 10 and 10.000 µg/ml. Within the group of saponins, the saponin Quil A® is the more preferred adjuvant. Saponin and vaccine components may be combined in ISCOMS® (EP 109.942, EP 180.564, EP 242.380).

Furthermore, peptides such as muramyldipeptides, dimethylglycine, or tuftsin, are often used as adjuvant, and mineral oil e.g. Bayol® or Markol®, vegetable oils or emulsions thereof and DiluvacForte® can advantageously be used.

It goes without saying that other ways of adjuvating, adding vehicle compounds or diluents, emulsifying or stabilizing a vaccine are also embodied in the invention. Such additions are for instance described in well-known handbooks such as: "Remington: the science and practice of pharmacy" (2000, Lippincot, USA, ISBN: 683306472), and: "Veterinary vaccinology", P. Pastoret et al. ed., 1997, Elsevier, Amsterdam, ISBN 0444819681).

The vaccine according to the invention can advantageously be combined with another antigen, or immunoactive component. This can also be added in the form of its encoding nucleic acid.

Therefore, in a still even more preferred embodiment the vaccine according to the invention is characterised in that it comprises an additional immunoactive component or a nucleic acid encoding said additional immunoactive component The additional immunoactive component(s) may be an antigen, an immune enhancing substance, and/or a vaccine; either of these may comprise an adjuvant.

The additional immunoactive component(s) when in the form of an antigen may consist of any antigenic component of human or veterinary importance. It may for instance comprise a biological or synthetic molecule such as a protein, a carbohydrate, a lipopolysacharide, a nucleic acid encoding a proteinacious antigen, or a recombinant nucleic acid molecule containing such a nucleic acid operably linked to a transcriptional regulatory sequence. Also a host cell comprising such a nucleic acid, recombinant nucleic acid molecule, or LRC containing such a nucleic acid, may be a way to deliver the nucleic acid or the additional immunoactive component. Alternatively it may comprise a fractionated or killed micro organism such as a parasite, bacterium or virus.

The additional immunoactive component(s) may be in the form of an immune enhancing substance e.g. a chemokine, or an immunostimulatory nucleic acid, e.g. a CpG motif. Alternatively, the vaccine according to the invention, may itself be added to a vaccine.

For instance a vaccine according to the invention can be combined with a preparation of a *Babesia* subunit vaccine protein, not being a protein of the 28 kDa protein family, to form a combination subunit vaccine against Babesiidae infection or associated clinical signs of disease.

In a yet even more preferred embodiment, the vaccine according to the invention is characterised in that said additional immunoactive component or nucleic acid encoding said additional immunoactive component is obtained from an organism selected from the group consisting of *Ehrlichia canis, Babesia gibsoni, B. vogeli, B. rossi, Leishmania donovani*-complex, Canine parvovirus, Canine distempervirus, *Leptospira interrogans serovar canicola, icterohaemorrhagiae, pomona, grippotyphosa, bratislava*, Canine hepatitisvirus, Canine parainfluenzavirus, rabies virus, *Hepatozoon canis* and *Borrelia burgdorferi*.

The protein of the 28 kDa protein family according to the invention, or the immunogenic fragment of said protein, the nucleic acid, cDNA, recombinant molecule, live recombinant carrier, and/or the host cells according to the invention for the first time allow the generation of specific antibodies against a protein of the 28 kDa protein family, or an immunogenic fragment thereof. This makes the vaccine according to the invention suitable as marker vaccine, as it allows the differentiation between parasite infected and vaccinated mammalian targets, through methods known in the art.

Alternatively, these specific antibodies may be used as a vaccine themselves, for so called "passive vaccination".

Therefore still another preferred embodiment relates to a vaccine, characterised in that it comprises an antibody against a protein according to the invention, or an antibody against an immunogenic fragment of said protein, or a combination thereof, and a pharmaceutically acceptable carrier.

A combination in a vaccine of an antigen 'loaded' with antibodies against that antigen is known in the art as a "complex" vaccine.

Still another aspect of the invention relates to a method for the preparation of a vaccine according to the invention, said method comprising the admixing of a protein according to the invention, or an immunogenic fragment of said protein, a nucleic acid, a cDNA fragment, a recombinant DNA molecule, a live recombinant carrier, or a host cell according to the invention, or a combination thereof, and a pharmaceutically acceptable carrier.

Yet another aspect of the invention relates to a method for the preparation of a vaccine according to the invention comprising the admixing of antibodies against a protein or an immunogenic fragment thereof according to the invention, and a pharmaceutically acceptable carrier.

As outlined above, a vaccine obtainable by the method according to the invention can equally be used as prophylactic and as therapeutic treatment, and will interfere both with the establishment and/or with the progression of an infection or its clinical signs of disease.

Therefore, a further aspect of the invention relates to the use of a protein according the invention or an immunogenic fragment of said protein, for the manufacture of a vaccine for prophylactic or therapeutic treatment of an infection or its clinical signs caused by an organism of the family Babesiidae.

Again a further aspect of the invention relates to a diagnostic test for the detection of a nucleic acid associated with an organism of the family Babesiidae, characterised in that the test comprises a nucleic acid, said nucleic acid being at least 70% homologous to the nucleic acid sequence depicted in SEQ ID NO: 1 or 3, or a nucleic acid that is complementary to said nucleic acid, wherein either of the nucleic acids have a length of at least 12, preferably 15, more preferably 18 nucleotides.

Yet a further aspect of the invention relates to a diagnostic test for the detection of antibodies against an organism of the family Babesiidae, characterised in that said test comprises a protein according to the invention or an immunogenic fragment of said protein, or a combination thereof.

For instance a Bc28.1 and/or a Bc28.2 protein or an immunogenic fragment of either is coupled to a solid phase carrier, this is incubated with a sample to be tested, is washed, and presence of bound antibodies is detected.

Still a further aspect of the invention relates to a diagnostic test for the detection of antigenic material from an organism of the family Babesiidae, characterised in that said test comprises an antibody against a protein according to the invention or an immunogenic fragment of said protein, or a combination thereof.

For instance antibodies against a Bc28.1 and/or a Bc28.2 protein or an immunogenic fragment of either are coupled to a solid phase carrier, this is incubated with a sample to be tested, is washed, and presence of bound protein is detected.

The invention will now be further described with reference to the following, non-limiting, examples.

EXAMPLES

Example 1

Identification of the Bc28 Multigene Family and Molecular Characterization of the Bc28.1 and Bc28.2 Coding Sequences 1.1. Techniques Used 1.1.1. General Techniques 1.1.1.1. Culture of *Babesia canis*

Isolates of *Babesia canis* (designated A, B, Castres, Gignac, 34.01 and Robin) were obtained from naturally infected dogs from different departments from France. They were maintained in in vitro culture according to Schetters et al. (1997, Parasitology, vol. 115, p. 485-493).

The A8 biological clone corresponded to a biological done of the isolate A from *B. canis* and was obtained following an adaptation of the cloning-dilution procedure described for malaria parasites (Walliker & Beale, 1993, Meth. in Molec. Biol., vol. 21, p. 57-66).

1.1.1.2. DNA Sequencing

Nucleotide sequencing was performed using the dideoxy chain termination method from alkali-denaturated double-strand templates according to Sanger et al. (1977, Proc. Natl. Acad. Sci. USA, vol. 74, p. 5463-5467) by Genome Express S.A. (Zone Astec, Grenoble, France) on both strands of the selected plasmids using T3 and T7 universal primers and various oligonucleotides derived from sequences of each strand already established.

1.1.1.3. DNA Primers

DNA primers used for isolating genomic fragments, for generation of probes and for PCR reactions are disclosed in Table 5, with reference to their respective SEQ ID number. All primers were synthesized by Sigma-Genosys (Cambridge, UK).

TABLE 5

DNA primers used during the course of the experiments

| Name | Sequence (in 5' → 3' orientation) | SEQ ID NO |
|---|---|---|
| pr3 | TGATGAAGCCGGCAAGAAGGT | 5 |
| E4 | TACATGATACCGAATTCAATGG | 6 |
| RT1 | TTACATCGTTGAGCTCAGCTACCTTGA | 7 |
| Inv5 | CCATGGATTCAAGGTAGCTGAG | 8 |
| 5'UTR | AGTCGATACCTCCGAGAATAG | 9 |
| Fspe3 | ACTGAGGATGAGAACAGGGATAGT | 10 |
| Cons3.1 | CATGGATTCAAGGTAGCTGAG | 11 |
| Rspe4 | GACCACAACCGCGACGGCGGCAAC | 12 |
| Rspe3G | GAGCTCATTGAGGAGTACAGG | 13 |
| Rspe3C | CATTACGCCCACAAATAGTCA | 14 |
| 3.1expfor | ATTTTGGTTCGTGGATCCACGTGCACTGAGGAT | 15 |
| 3.1exprevC | CCACAAATAGTCAAGCTTAACCTCTAA | 16 |
| 3.1exprev | GAATGAGAATCCAAGCTTCTTACCCTTGGC | 17 |
| Gene-Racer® 5' | CGACTGGAGCACGAGGACACTGA | 18 |
| Gene-Racer® 3' | GCTGTCAACGATACGCTACGTAACG | 19 |

1.1.1.4. Genomic DNA Extraction, Southern Blot and Chromosomal Analysis

Genomic DNA extraction from *B. canis* in vitro cultures or from field samples of infected dog blood was performed on 200 µl of blood using Nucleospin® column according to the manufacturer (Macherey-Nagel). Southern blot experiments were performed using standard procedures described in Sambrook & Russell (supra).

The preparation of agarose plugs containing intact or NotI-digested chromosomes of *B. canis* and their separation by pulse-field gel electrophoresis (PFGE) were performed as described in Depoix et al. (2002, Parasitology, vol. 125, p. 313-321).

The Bc28 probe that was used for the DNA hybridisation experiments was obtained by performing a PCR with the combination of primers Fspe3 and Rspe4 using the plasmid carrying the Bc28.1 cDNA as DNA template. The Bc28 probe was labelled using the Nick Translation kit according to the manufacturer's instructions (Boehringer Mannheim) and as described in Depoix et al. (supra).

1.1.1.5. RNA Extraction and Northern Blot Analysis

Total RNA extraction, mRNA purification and RNA hybridisation were performed as described in Drakulovski et al. (2003, Infect. Immun., vol. 71, p. 1056-1067). The digoxigenin (DIG)-11-UTP-labelled Bc28 antisense riboprobe (complementary mRNA sequence obtained from using the primers Fspe3 and Rspe4) was synthesized according the DIG High Prime® DNA labelling kit (Boehringer Mannheim).

1.1.1.6. PCR Amplification

Amplifications were performed in a PTC-100® Programmable Thermal Controller (MJ Research, Inc) as described in Depoix et al. (supra), using Accu Taq® DNA polymerase (Sigma).

1.1.2. Identification of the Bc28.2 Genomic Fragment from B. canis by PCR with Primers Derived from the Bd37 cDNA of B. divergens Two primers, pr 3 and E4, were used in a PCR set-up on genomic DNA from isolate A of *B. canis*. The conditions of annealing were the following: the annealing temperature was increased by 2° C. per cycle from 45° C. to 55° C. and then 25 cycles of amplification were performed at 55° C. These conditions allowed to amplify a 500 bp genomic fragment, that was designated Bc28.2. The PCR fragment was then cloned in the pCRII-TOPO® cloning vector according the manufacturer's instruction (Invitrogen), and sequenced.

1.1.3. Cloning of the Complete Bc28.1 cDNA Sequence of B. canis

The complete sequence from the cDNA Bc28.1 was determined by RT-PCR using primers derived from the sequence of the Bc28.2 genomic fragment for the first retrotranscription step. For the RT-PCR experiment, the GeneRacer® protocol was applied according to the manufacturer's instructions (Invitrogen) on intact mRNA from *B. canis*. The 5' end sequence of the cDNA (clone 5'-Bc28.1, 5'-RACE PCR product) was determined by using the reverse primer RT1 for the first retrotranscription step. The 3'-end of the cDNA Bc28.1 (clone 3'-Bc28.1, 3'-RACE PCR product) was obtained using the forward primer Inv5, derived from the sequence of the clone 5'-Bc28.1, in the first retrotranscription step of the protocol. The 5' and 3' ends of the cDNA Bc28.1 were then amplified by PCR using a primer-couple corresponding to the one that was used first for each of the retrotranscription steps and with the forward GeneRacer® 5' primer (5'-CGACTGGAGCACGAGGACACTGA-3') or the reverse GeneRacer® 3' primer (5'-GCTGTCAACGATACGCTACGTAACG-3') (Table 5) provided in the GeneRacer™ kit (Invitrogen). In both cases, a single PCR product was obtained using Accu Taq® DNA polymerase (Sigma). These fragments were cloned in pCRII-TOPO, and sequenced. Sequences from the clones 5'-Bc28.1 and 3'-Bc28.1 were assembled to form the complete sequence of the Bc28.1 cDNA from *B. canis*.

1.1.4. Cloning of the Encoding Regions from the Bc28.1 and Bc28.2 Coding Sequences from B. canis A specific reverse primer from the Bc28.1 and Bc28.2 nucleotide sequences was designed in order to sequence their corresponding genomic copy. The complete open reading frame (ORF) from the coding sequence Bc28.2 was amplified by PCR with the forward 5'UTR primer derived from the 5' end of the Bc28.1 cDNA sequence and the reverse Rspe3G primer that specifically hybridises to the 3' end of the genomic sequence of Bc28.2. The sequence of the complete ORF from the Bc28.1 coding sequence was amplified by PCR with the 5'UTR primer and with the reverse Rspe3C primer that specifically hybridises to the 3' end of the Bc28.1 cDNA sequence. The PCR amplifications were performed using the genomic DNA from the biological clone A8 from *B. canis* as DNA template. Amplifications were performed with the following conditions: a 3 min step of denaturation at 94° C., a 3-step cycling program consisting of 1 min denaturation at 94° C., 1 min annealing at 55° C., and 1 min of extension at 72° C., finally followed by a 5 min step at 72° C. The PCR fragments were then cloned in pCRII-TOPO and sequenced.

1.1.5. Analysis of the Polymorphism of the Bc28.1 and Potential Bc28.2 Coding Sequences The Bc28.1 and Bc28.2 coding sequences from the French laboratory *Babesia canis* isolates B, Robin, Castres, Gignac and 34.01 were amplified by PCR with the primer-couples Fspe3/Rspe3C or Fspe3/Rspe3G and a restriction map based on 5 restriction enzymes (AluI, EcoRI, HinfI, MboI and MspI) was calculated for both genes. On the basis of the deduced restriction maps from the Bc28.1 coding sequence, the entire coding region of Bc28.1 from the French laboratory *Babesia canis* isolates B, Robin, Castres and 34.01 were amplified by PCR with the primer-couples 5'UTR/Rspe3C, and cloned and sequenced as described above (§ 1.1.2).

1.2. Results:

1.2.1. Identification of a Genomic Fragment from B. canis by PCR

Two primers, pr 3 and E4 were used in a PCR set-up with an increasing annealing temperature from 45 to 55° C. on genomic DNA from *B. canis* (FIG. 5).

It allowed the amplification of a fragment of approximately 500 bp (FIG. 5, lane 2; indicated with a dot). This amplification was specific since the test of each of the primers separately in control amplifications was negative (FIG. 5, lanes 5 and 6).

This clone, Bc28.2, hereafter called Bc28.2 (see below) was cloned in a pGEX® vector to be able to express a GST fusion-protein.

1.2.2. Identification of the Bc28 Multigene Family and Cloning of the Bc28.1 and Bc28.2 Coding Sequences

1.2.2.1. Cloning of the Complete Bc28.1 cDNA

In order to find a complete cDNA sequence corresponding to the genomic fragment of Bc28.2, an RT-PCR experiment on intact mRNA from *B. canis* was performed using the GeneRacer protocol. Firstly, a single 5'-RACE PCR product was obtained by performing the first retrotranscription step with the reverse primer RT1 derived from the sequence of the genomic clone Bc28.2 followed by a PCR with the same RT1 primer and the forward GeneRacer 5' primer provided in the Gene Racer kit. Then, a single 3'-RACE PCR product was obtained using the forward primer Inv5, derived from the deduced sequence of the 5'-RACE PCR product, in the first retrotranscription step of the protocol followed by a PCR with the same primer and the GeneRacer 3' primer provided in the kit. Sequences from the 5'-RACE and 3'-RACE PCR products were assembled and constitute the complete sequence of the Bc28.1 cDNA. This cDNA contained a 1039 bp sequence with a poly(A)20 tail and with an ORF of 753 nucleotides. Within the segment 5'UTR/Rspe3C of the cDNA, this ORF starts with an ATG initiation codon at nucleotide (nt) position 50 (or nt position 71 from the entire cDNA) and ends with a TAA stop codon at nucleotide position 820 (or nt position 841 from the entire cDNA).

Alignment of the Bc28.2 genomic fragment sequence with the complete sequence of the deduced cDNA revealed a significant identity in the region of primers RT1 and Inv5 between the two sequences (i.e. in the 5' end of the Bc28.2 sequence). However, their 3' ends were found to be very distant, suggesting the presence of at least 2 related genomic copies in the genome of *B. canis* for this gene. As the cDNA sequence encodes a poly-peptide of around 28 kDa, and because its 3' end was distant from the related genomic done, it was designated Bc28.1 whereas the related genomic done was designated Bc28.2.

1.2.2.2. Design of Primer for Specific PCR Amplification of Bc28.1 and Bc28.2 Coding Sequences As the comparison of the nucleotide sequences from the cDNA Bc28.1 and the genomic clone Bc28.2 suggested two related genomic copies in the genome of the parasite, specific primers able to amplify each of the copies were designed. The two sequences being the most distant in their 3' end, the primers Rspe3G and Rspe3C, respectively designed to amplify the Bc28.2 and Bc28.1 coding sequence, were therefore selected from this region (FIG. 3). To demonstrate their specificity for each coding sequence, they were tested by PCR in combination with the primer Cons3.1 (FIG. 3) that is located in the 5' end of the Bc28.2 sequence and that hybridises in a conserved region of the two sequences. Moreover, to certify that the two copies of related coding sequences do not derive from two subpopulations of B. canis in the isolate A, the PCR's were performed using the genomic DNA from a biological clone, clone A8 of B. canis.

Figure 6:
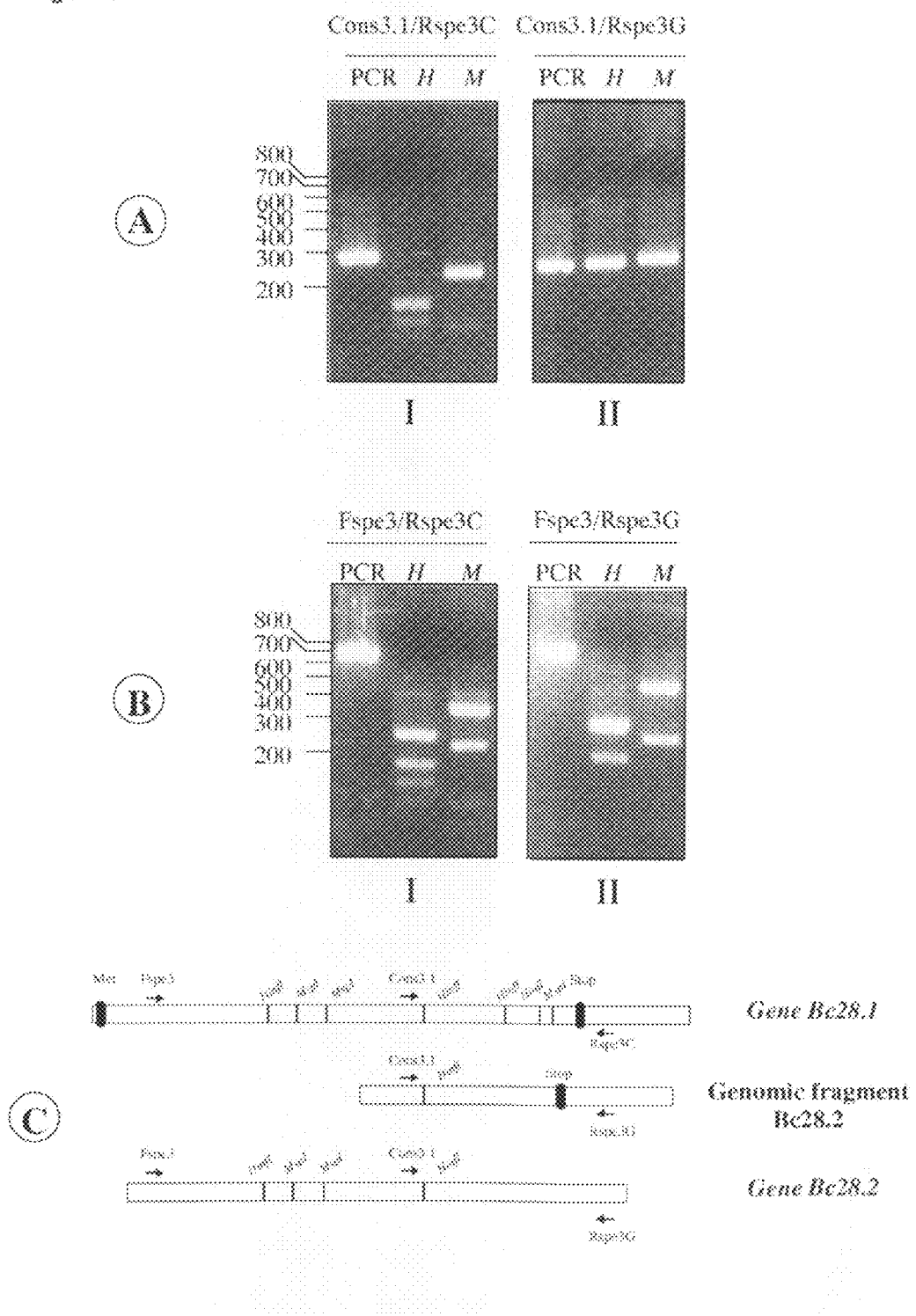

The combinations of primers Cons3.1/Rspe3G and Cons3.1/Rspe3C allowed the amplification of a genomic fragment of some 300 bp for both combinations of primers (FIG. 6, A, I and II, lanes PCR). To certify that the primers Rspe3G and Rspe3C hybridise specifically to the Bc28.2 and Bc28.1 coding sequence respectively, the amplified fragments were digested by the restriction enzymes HinfI or MstI (FIG. 6, A, I and II, lanes H and M). Comparison of the restriction maps of the two sequences revealed the absence of two HinfI restriction sites (located at position 713 and 777 in the Bc28.1 sequence) and one MspI site (located at position 790 in the Bc28.1 sequence) in the 3' end of the Bc28.2 sequence (FIG. 6, C; compare the restriction maps from the Bc28.1 coding sequence and the Bc28.2 genomic fragment). As expected, the HinfI and MspI digestion of the amplimer Cons3.1/Rspe3C showed a digestion of the amplified fragment in 3 and 2 fragments (FIG. 6, A, I, lanes H and M, respectively). In contrast, the Cons3.1/Rspe3G PCR fragment was not digested by these two enzymes (FIG. 6, A, II, lanes H and M), demonstrating that the primers Rspe3G and Rspe3C specifically hybridise to the Bc28.2 and Bc28.1 coding sequences from the biological clone A8 from B. canis.

In order to analyse the 5' end of the Bc28.2 coding sequence, a similar PCR-RFLP was performed by using the combinations of primers Fspe3/Rspe3G and Fspe3/Rspe3C (FIG. 6, B, I and II). In both cases, the amplimers were digested by the two enzymes and the sizes of the fragments resulting from these digestions show that the 5' end of the Bc28.2 and Bc28.1 coding sequences are conserved (FIG. 6, C; compare the restriction maps from the Bc28.1 and Bc28.2 coding sequences). Indeed, the 5' end of the Bc28.2 coding sequence contained the single HinfI site (located at position 308 of the Bc28.1 coding sequence) and two MspI sites (located at positions 367 and 412 of the Bc28.1 coding sequence) from the Bc28.1 coding sequence in a conserved position.

In conclusion: two related Bc28 coding sequences are present in the genome of B. canis. Specific primers able to analyse each of the two copies are disclosed. The restriction map comparison shows that both copies contain a conserved 5' end whereas their 3' ends are very distant.

1.2.2.3. Hybridisation Experiments with a Bc28.1 Probe

The probe used for hybridisation experiments (Southern blot, Northern blot and PFGE analysis) (FIG. 7) corresponded to the coding region of Bc28.1 cDNA located between primers Fspe3 and Rspe4 (FIG. 3).

1.2.2.3.1. The Bc28.1 Coding Sequence Belongs to a Multigene Family.

Figure 7:
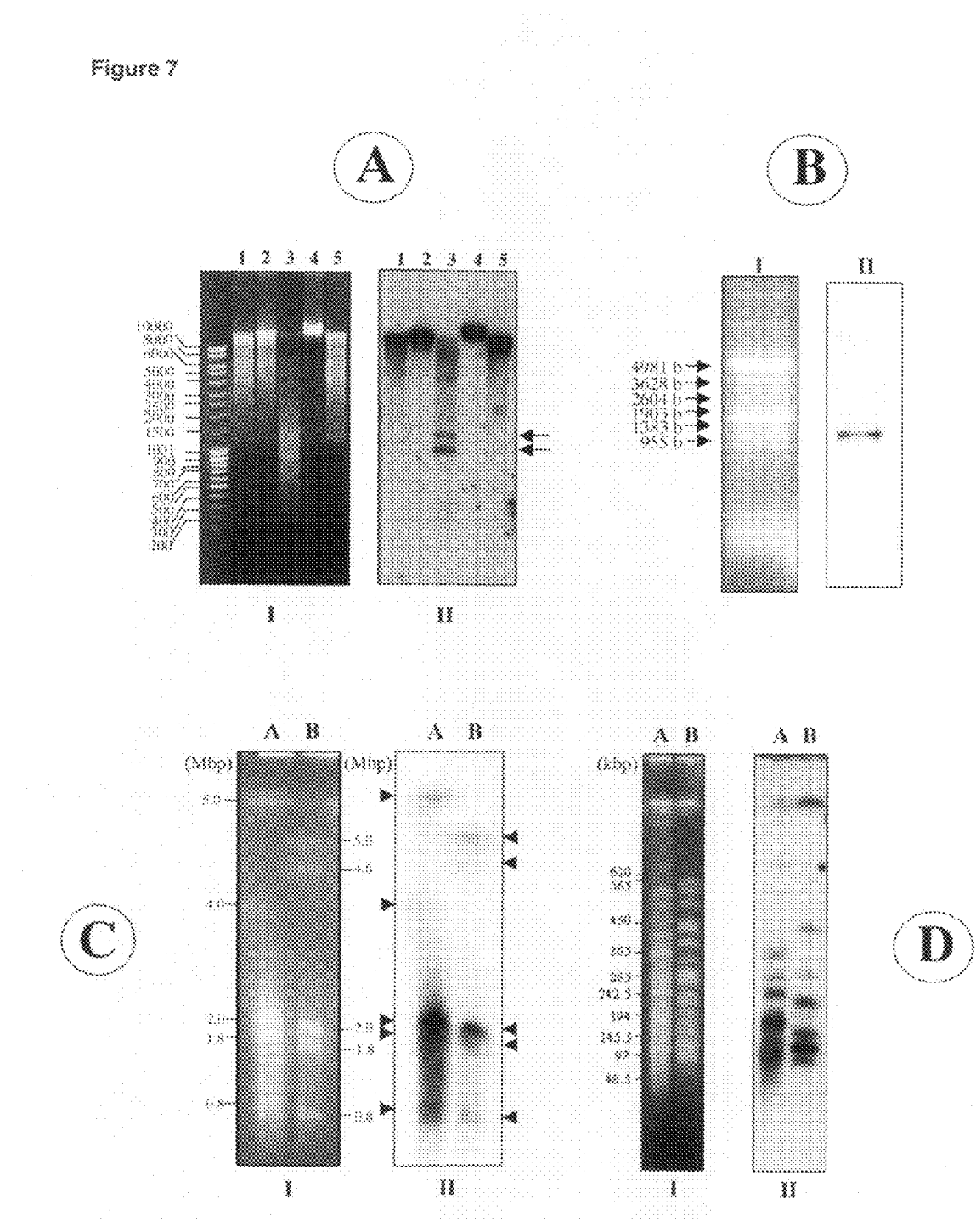

First, the results of the Southern blot experiment revealed two hybridised fragments of some 1200 and 1400 bp when the genomic DNA of B. canis was digested with the RsaI enzyme (FIG. 7, A, II, lane 3, indicated by arrows). As no RsaI restriction site is present in the restriction map of the Bc28.1 cDNA, it demonstrates the presence of at least two related genomic copies, in agreement with the identification of the related sequences of Bc28.1 and Bc28.2.

Then, hybridisation experiments were performed with the Bc28.1 probe on the entire (FIG. 7, C, II) or NotI-digested (FIG. 7, D, II) chromosomes from the Babesia canis isolates A (FIG. 7, C and D, II-A) and B (FIG. 7, C and D, II-B), which had been separated by PFGE. This indicated that at least 10 genomic copies of related Bc28 coding sequences exist in the genome of B. canis (FIG. 7, D, II) and that these copies are located on the 5 chromosomes from the parasite, in both isolates (FIG. 7, C, II). The difference in sensitivity of the hybridisation signals, both for isolates A and B, shows a sequence polymorphism between the different related Bc28 sequences for a given isolate in that family.

1.2.2.3.2. Northern Blot Analysis

Whereas previously described data show there are at least 10 members related to the Bc28.1 cDNA, hybridisation of the probe on total RNA from B. canis revealed a single band of around 1.1 kb mRNA, in agreement with the size of the Bc28.1 cDNA sequence (FIG. 7, B, II). Moreover, whereas our data show that the two related coding sequences Bc28.1 and Bc28.2 encode different products (28 and 45 kDa, see example 2, section 2.2.1.), no larger mRNA that encoded the 45 kDa was detected.

In conclusion: the Bc28.1 and Bc28.2 coding sequences belong to a multigene family that is composed of at least 10 members located on the 5 chromosomes of B. canis. A single mRNA was detected that encodes a 28 kDa protein, corresponding to the Bc28.1 copy. The larger mRNA encoding the 45 kDa protein corresponding to the band recognized by the α-GST-Bc28.2 antiserum could not be detected; the small amount of protein detected in immunoprecipitation experiments indicates this mRNA is transcribed at a very low level, additionally it shows that the transcription of members from the Bc28 family is regulated.

1.2.2.4. Cloning of the Bc28.2 Coding Sequence within the Biological Clone A8 from B. canis and Comparison of its Sequences with the Bc28.1 Coding Sequence Specific genomic fragment from the Bc28.2 coding sequence was amplified by PCR using the genomic DNA from the biological clone A8 from B. canis as DNA template with the combinations of primers 5'UTR/Rspe3G. The genomic fragment was cloned and sequenced. The genomic sequence Bc28.2 was aligned and compared with the equivalent Bc28.1 coding sequence amplified with the combination of primer 5'UTR/Rspe3C both at the nucleotide (FIG. 3) and amino acid levels (FIG. 1).

1.2.2.4.1. Comparison at the Nucleotide Level

Such a PCR amplified 845 and 852 nucleotide length sequences for the Bc28.2 and Bc28.1 genomic sequence, respectively (FIG. 3). Comparison of the Bc28.1 cDNA and genomic equivalent sequences indicated that no intronic sequence was found in the Bc28.1 coding sequence. The percentage of identity, determined using the BlastN program as described, between the Bc28.1 and Bc28.2 sequences at the nucleotide level was 94% when the comparison was performed with all 845 nucleotides from the two sequences (Table 3). However, and as suggested by the previously described comparative restriction map analysis using PCR-RFLP experiment (FIG. 6, C), comparison of the two nucleotide sequences revealed a strong conservation at the 5' end whereas their 3' end was polymorphic (FIG. 3). Indeed, whereas the percentage of identity at the nucleotide level was of 97% when the comparison was performed with the first 652 nucleotides from the two sequences, the comparison of the remaining 193 nucleotides from their 3' end revealed only 81% identity (Table 3).

1.2.2.4.2. Comparison of Restriction Maps of the Bc28.1 and Bc28.2 Coding Sequences Specific genomic fragments corresponding to the coding region of the Bc28.1 and Bc28.2 coding sequences between the primers Fspe3 and Rspe3C or Rspe3G were amplified by PCR using the genomic DNA from the biological done A8 from B. canis as DNA template. These genomic fragments corresponding to the two copies from the biological clone A8 were digested by various restriction enzymes in order to compare the restriction maps of the Bc28.1 coding sequence and of the Bc28.2 coding sequence (FIG. 8, A) within the A8 biological clone.

Figure 8:
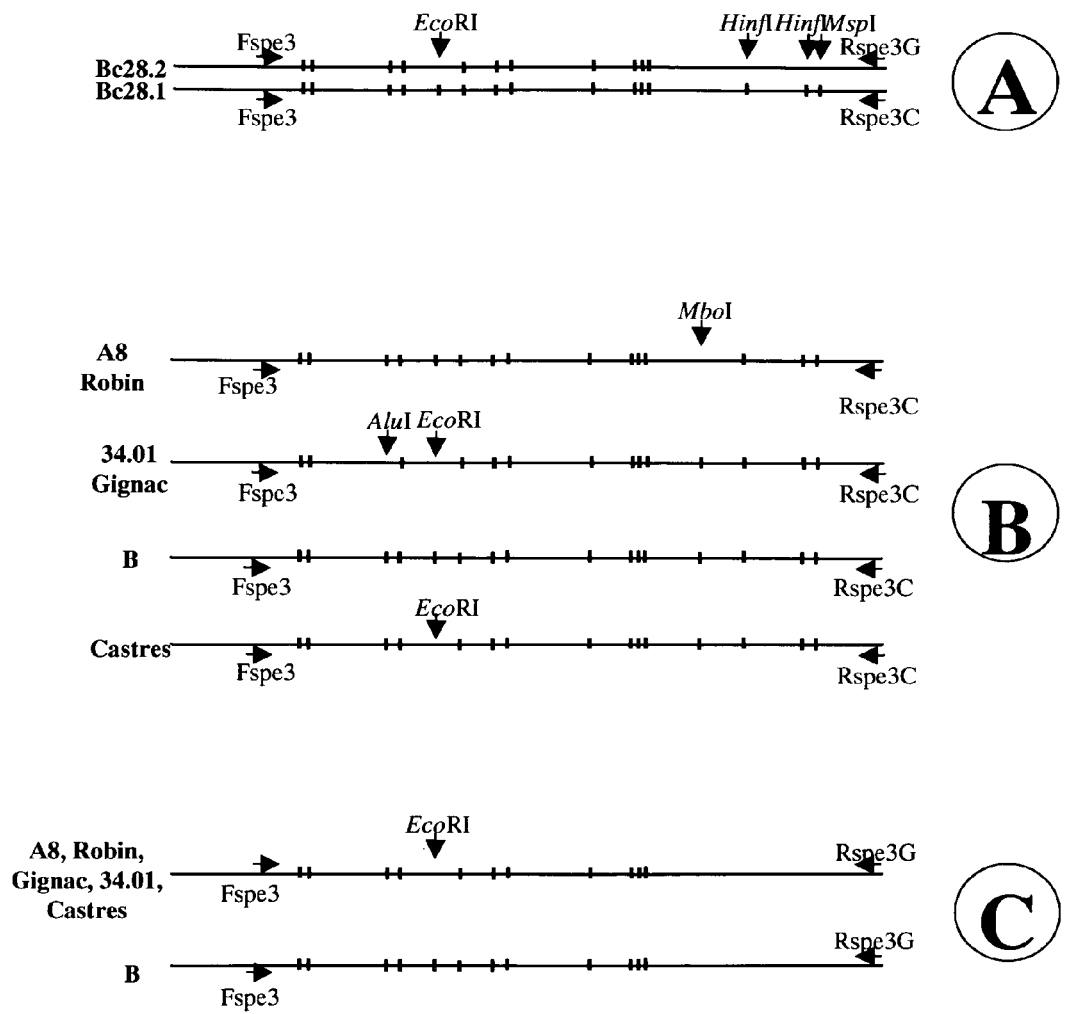

As previously showed, such PCR-RFLP analyses revealed that both copies shared some restriction sites, especially in their 5' end. The main differences between the two copies are the lack of two HinfI and a single MspI restriction sites at the 3' end of the Bc28.2 coding sequence. At the 5' end of the two copies, the only difference is the lack of an EcoRI restriction site at the 5' end of the Bc28.2 coding sequence (FIG. 8, A).

1.2.2.4.3. Comparison at the Amino Acid Level

Comparative analysis of the products encoded by the coding sequences of Bc28.1 and Bc28.2 was performed (FIG. 1). An ORF of 244 and 256 amino acids was predicted for the Bc28.2 and Bc28.1 genomic sequences, respectively (FIG. 1). The two ORF's were different in size since, whereas both begin at the same nucleotide position (position 50), the Bc28.2 ORF finishes with a TGA stop codon at position 784 and the Bc28.1 ORF finish with a TAA stop codon at position 820 of their nucleotide sequences (FIG. 3). As previously described, the percentage homology between the two predicted proteins was determined with the complete sequence or with the N-terminal or C-terminal of the proteins (Table 1), using the BlastP program. Comparison of the two complete proteins (on 244 residues) revealed a global homology of 91%. As previously described, whereas the N-terminal part of the two proteins was found to be very conserved (97% homology between the first 180 amino acids from the two proteins), their C-terminal parts were found to be more polymorphic, with an homology of 73% in the last 64 amino acids.

1.2.2.4.4. Predictive Analysis of the Bc28.1 and Bc28.2 Encoded Products

The proteins encoded by the Bc28cDNA.1 has a predicted molecular weight of 28.3 kDa (and a pI of 6.24) whereas the protein encoded by the Bc28.2 coding sequence has a predicted molecular weight of 27.5 kDa (and a pI of 9.30).

Figure 9:
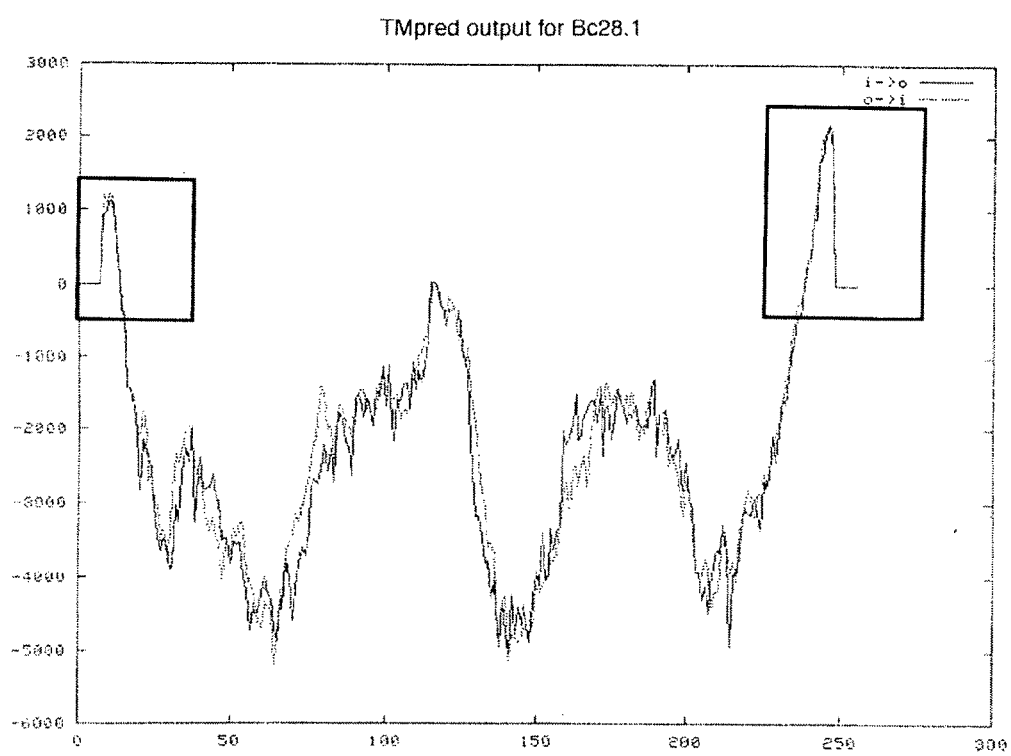

Analysis of the hydrophobicity profile (FIG. 9) revealed no internal hydrophobic sequence for both proteins. However, they both shared an N-terminal hydrophobic segment that corresponds to a signal peptide. A cleavage site is present between the $A^{16}$ and $V^{17}$ residues. In contrast to the Bc28.2 protein, the Bc28.1 protein contained another hydrophobic segment located at the C-terminal end of the protein (FIG. 9). This $G^{236}$-$V^{256}$ hydrophobic segment is a GPI anchor.

In conclusion: The two genomic copies Bc28.1 and Bc28.2 from the multigene family are predicted to encode products of around 28 kDa. Both proteins contain a cleavable signal peptide at their N-terminal parts. A GPI anchor is present on the C-terminal part of the Bc28.1 protein, but not at the C-terminal part of the Bc28.2 protein. The two related Bc28.1 and Bc28.2 nucleotide sequences, like their deduced amino acid sequences, are strongly conserved in their 5' moiety, but are more polymorphic in their 3' moiety.

1.2.3. Polymorphism of the Bc28.1 and Bc28.2 Coding Sequences Between Geographically and Genetically Disparate B. canis Field Isolates 1.2.3.1. Comparison of Restriction Maps of the Bc28.1 and Bc28.2 Coding Sequences by PCR-RFLP Specific genomic fragments corresponding to the coding region of the Bc28.1 and Bc28.2 coding sequences between the primers Fspe3 and Rspe3C or Rspe3G were amplified by PCR using the genomic DNA from the French B. canis isolates A8, B, Castres, Gignac, 34.01 and Robin as DNA template. These genomic fragments corresponding to the two copies from the isolates A8, B, Robin, Castres, Gignac and 34.01 were digested by various restriction enzymes in order to compare the restriction maps of the Bc28.1 and Bc28.2 coding sequences (FIG. 8, B, C respectively) between isolates.

1.2.3.1.1. Comparison of the Bc28.1 Coding Sequence Restriction Maps

This PCR-RFLP analysis of the PCR fragments amplified with the combination of primers Fspe3/Rspe3C revealed an important conservation of the restriction maps between the Bc28.1 coding sequences from the various available isolates (FIG. 8, B).

1.2.3.1.2. Comparison of Restriction Maps of the Bc28.2 Coding Sequence

Like for the Bc28.1 coding sequence, the PCR-RFLP analysis of the PCR fragments amplified with the combinations of primers Fspe3/Rspe3G revealed an important conservation of the restriction maps between the potential Bc28.2 coding sequence from the various isolates (FIG. 8, C).

1.2.3.2. Sequencing of the Bc28.1 Coding Sequences from Different Isolates of B. canis To confirm the conservation of the Bc28.1 coding sequences between geographically and genetically disparate B. canis field isolates, the coding region (i.e. between primers 5'UTR and Rspe3C) of the Bc28.1 coding sequence from the isolates A8, Robin, Castres, B and 34.01 were amplified by PCR, cloned, sequenced, aligned and compared both at the nucleotide (FIG. 4) and amino acid levels (FIG. 2).

1.2.3.2.1. Comparison at the Nucleotide Level

PCR with the of primer-couple 5'UTR/Rspe3C amplified a 852 nucleotide length genomic Bc28.1 sequence for the isolates B, Robin and A, and a 849 nucleotide length genomic Bc28.1 sequence for the isolates 34.01 and Castres (FIG. 4). The percentage of identity at the nucleotide level between these Bc28.1 sequences, in pairwise alignments using the BlastN program, is comprised between 100% (A8 and Robin are the closest) and 97% (Table 4), indicating a strong conservation of the coding sequence between isolates of B. canis.

1.2.3.2.2. Comparison at the Amino Acid Level

Comparative analysis of the protein encoded by the Bc28.1 coding sequence from these different isolates was performed (FIG. 2, Table 2). An ORF of 256 amino acids was obtained for the isolates B, A and Robin whereas this ORF was 255 amino acids for the isolates 34.01 and Castres (FIG. 2). As previously described, the homology between the different Bc28.1 proteins, determined in pairwise alignments using the BlastP program, was very strong, between 100% (A and Robin) and 97% (Table 2).

In conclusion: analysis of the restriction maps from the Bc28.1 and Bc28.2 coding sequences from B. canis show a strong conservation of each sequence between the different isolates. As all these isolates were collected in France, this conservation might be due to the fact that these isolates all came from the same country, even if they originate from different regions. However, evidence suggested that these isolates are genetically disparate *B. canis* field isolates. Indeed, their chromosomal content analysis revealed that all these isolates have a specific chromosomal profile. Moreover, the analysis of the polymorphism of the Bc28.1 coding sequence by a PCR-RFLP experiment was performed on around 60 blood samples collected from infected dogs in all parts of France and in other European countries (Germany and Hungary). Such analysis with field samples did not show the identification of other restriction patterns than the ones described in this report, in agreement with a good conservation of this coding sequence between geographically and genetically disparate *B. canis* field isolates.

This conservation between the Bc28.1 coding sequences and deduced proteins for the different isolates was confirmed by sequencing. It revealed an homology between the different coding sequences (identity) and encoded proteins of over 96%.

Example II

Biochemical Characterization of the Bc28.1 and Bc28.2 Proteins 2.1. Techniques Used 2.1.1. Expression and Purification of GST-Bc28.2 and His-Bc28.1 Recombinant Proteins in *E. coli*.

2.1.1.1. Production of His-Tagged Bc28.1 Recombinant Proteins

Two recombinant Histidine tagged-Bc28.1 proteins, without the N-terminal part of Bc28.1, with and without GPI anchor at the C-terminal part, were designated His-Bc28.1C ($V^{16}$-$V^{256}$) and His-Bc28.1 ($V^{16}$-$K^{233}$) respectively. These proteins were purified by affinity chromatography on Ni-NTA beads under denaturing conditions for the His-Bc28.1C protein or under native conditions for the His-Bc28.1 protein, according to the manufacturer's instructions (Qiagen).

2.1.1.1.1. His-Bc28.1C

The Bc28.1C cDNA sequence without its N-terminal part (nt 104-865 from the entire cDNA or nt 83-844 from the 5'UTR/Rspe3c segment) was amplified by PCR using a cDNA library from *Babesia canis* (isolate A) as DNA template. This cDNA library was constructed, as described in Carret et al. (1999, Eur. J. Biochem., vol., 265, p. 1015-1021), with the ZAP Express® cDNA Gigapack II® Gold Cloning kit (Stratagene). PCR was performed using internally modified primers 3.1expfor and 3.1exprevC. These primers contain respectively a BamHI and HindIII restriction site to allow the cloning of the amplified sequence in BamHI/HindIII digested pQE-30 vector (Qiagen) in frame with the His-tag present in that plasmid. Then, the PCR product was purified by agarose gel electrophoresis, by loading onto a 0.8% agarose gel (electrophoresis grade, Eurobio, France) running in 0.5× TAE (made from 25× TAE stock solution, Euromedex) at 100V. The band corresponding to the desired product was excised from the gel and the DNA was isolated from the gel slices using a gel-extraction Spin kit® (Q-Bio-Gene). It was then digested with BamHI and HindIII and gel purified again. The resulting fragment was ligated into dephosphorylated BamHI/HindIII digested pQE-30 vector, by ligation with T4 DNA ligase (MBI Fermentas, France) in 1× ligase buffer (MBI Fermentas) supplemented with 2 mM ATP (Sigma), at room temperature during 3 hours. The ratio vector:insert was usually 1:3, wherein the amount of digested vector used was between 0.5 and 1 µg.

The ligation mix was transformed into JM109 supercompetent® *E. coli* cells (Promega). These cells were plated on ampicillin containing agar plates, and colonies were checked for expression of Bc28.1C protein by protein mini-expression and the recombinant protein (His-Bc28.1C; nt 118-838 from the entire cDNA, or nt 98-817 from the 5'UTR/Rspe3C segment; $V^{16}$-$V^{256}$) was purified by affinity chromatography on Ni-NTA beads under denaturing conditions. Briefly, a small scale (5 ml) bacterial culture in LB medium was initiated by 1-fold dilution of an overnight culture. After 2 h incubation at 37° C. with shaking, recombinant protein expression was induced by addition of 1 mM IPTG (Euromedex). After 3 h of induction, cells were harvested by centrifugation (15 min, 4000×g) and lysed in 1 ml of denaturing buffer (8 M urea, 1% v/v Triton X-100, 50 mM Tris, pH 8). Lysates were sonicated for 2 minutes with 2 second pulse-pause cycle on ice, and centrifuged (10 min, 15000×g). Clarified lysates were incubated 20 min on ice with occasional shaking in the presence of 50 µl Ni-NTA agarose resin (Qiagen). Loaded resin was washed thrice with 1 ml of washing buffer (8 M urea, 1% v/v Triton X-100, 50 mM Tris, pH 6.3) and protein eluted with elution buffer (8 M urea, 1% v/v Triton X-100, 50 mM Tris, pH 4.5). The presence of recombinant protein was assessed by SDS-PAGE in 12% polyacrylamide gel, which was stained with Coomassie Brilliant blue (CBB) and by Western blot with anti-His tag monoclonal antibody (Qiagen).

Prior to large scale production of His-Bc28.1C protein, one colony positive for Bc28.1C expression was selected to check the correct in frame fusion of the Bc28.1C core with the 6×His linker.

In conclusion: a bacterial culture was produced by overnight incubation in 2 ml of LB medium, at 37° C. with shaking, and plasmid pQE-His-Bc28.1C was isolated using the JetQuick® miniprep kit (Q-Bio-Gene). The correct in frame fusion of the Bc28.1C core with the 6× His linker was checked by sequencing. Once checked, the Bc28.1C protein was produced to a larger scale with the same protocol.

2.1.1.1.2. His-Bc28.1

The Bc28.1 cDNA sequence deleted from both the N and C-terminal parts (nt 104-787 from the entire cDNA or nt 83-766 from the 5'UTR/Rspe3C segment) was amplified by PCR using internal modified primers 3.1expfor, and 3.1exprev as described above. These primers respectively contain BamHI and HindIII restriction sites to allow the cloning of the amplified sequence in BamHI/HindIII digested pQE-30 vector in frame with the His-tag. The ligation mix was transformed into *E. coli* cells, cells were plated, and colonies were checked for expression of Bc28.1 protein by protein mini-expression, as described above. The recombinant protein (His-Bc28.1; nt 118-769 from the entire cDNA or nt 83-766 from the 5'UTR/Rspe3C segment; $V^{16}$-$K^{233}$) was purified by affinity chromatography on Ni-NTA beads under native condition. Briefly, a bacterial culture in LB medium was initiated by 10-fold dilution of an overnight culture, after 2 h incubation at 37° C. with shaking, recombinant protein expression was induced by addition of 1 mM IPTG (Euromedex). After 3 h of induction, cells were harvested by centrifugation (15 min, 4000×g) and resuspended in Histag lysis buffer containing 1% Triton X-100, 1 mg/ml lysosyme and 1 mM phenyl-methyl-sulphonyl fluoride (PMSF) (Sigma). Lysate was stored at −80° C. until use. After thawing, 500 U DNAse I enzyme (Life Technologies) was added, incubated 20 min on ice, next the suspension was sonicated on ice for 2 min with 2 second pulse-pause cycles. The sonicate was centrifuged (20 min, 9000×g) and the supernatant was filtered sequentially through 1.2, 0.45 and finally 0.22 μm filters (Pall Gelman, France). Finally, the filtrate was separated on FPLC $Ni^{2+}$ HiTrap® columns (Pharmacia). The loaded column was washed with Histag lysis buffer supplemented with 20 mM imidazole (Sigma). The recombinant Bc28.1 protein was finally eluted in Histag lysis buffer containing 200 mM imidazole.

The His-Bc28.1C protein was purified under denaturing conditions and was injected into a rabbit to produce a polyclonal serum (α-His-Bc28.1C) (section 2.1.2.), which antiserum was used for invasion reduction assays (Example 4).

The His-Bc28.1 protein was purified under native conditions and was used for the erythrocyte binding assay (section 2.1.4.).

2.1.1.2. Production of a GST-Tagged Bc28.2 Recombinant Protein

A GST-Bc28.2 recombinant protein was produced by subcloning the 3' end part of the Bc28.2 coding sequence in frame with GST. Firstly, the recombinant PCRII-TOPO cloning vector carrying the partial Bc28.2 sequence was digested with the restriction enzymes BamHI/EcoRI (the 5'BamHI site is from the vector and the 3'EcoRI site is from the primer E4). This BamHI/EcoRI fragment was purified by agarose gel electrophoresis as previously described, it was excised from the gel and the DNA was isolated from the gel slices using a gel-extraction Spin kit® (Q-Bio-Gene). The resulting fragment was ligated into the dephosphorylated BamHI/EcoRI digested pGEX-4T3 vector (Amersham-Pharmacia), by ligation with T4 DNA ligase (MBI Fermentas, France) in 1× ligase buffer (MBI Fermentas) supplemented with 2 mM ATP (Sigma), at room temperature during 3 hours. The ligation mix was transformed into *E. coli* BL21 cells (Novagen) and these cells were plated on ampicillin containing agar plates overnight. A positive colony was selected using PCR with the primers pr 3/E4 and it was induced by IPTG to check for expression of GST-Bc28.2 protein. Thus, the positive bacterial culture was grown overnight and diluted 1:10 with LB medium supplemented with ampicillin at 50 μg/ml. The culture was incubated for 1 h at 37° C. and then incubated with 0.1 mM IPTG during 3 h. Cells were harvested by centrifugation (15 min, 4000×g) and lysed by sonication in MTPBS (150 mM NaCl, 16 mM $Na_2HPO4$, 4 mM $NaH_2PO4$, pH 7.3) with 1% Triton X-100. The recombinant protein was purified by affinity chromatography on glutathione-agarose beads (Sigma) and eluted by competition with reduced glutathione, i.e. in a buffer containing 50 mM Tris (pH 8) with 45 mM glutathione (Smith & Johnson, 1988, Gene, vol. 67, p. 31-40).

2.1.2. Immunisation

A polyclonal antiserum raised against the GST-Bc28.2 or against the His-Bc28.1C protein was produced respectively in mice and in rabbits according to E. Harlow & D. Lane ("Antibodies: a laboratory manual", ISBN 2907516159). Rabbits (New Zealand White) were immunized with 50 μg of purified His-Bc28.1C recombinant proteins emulsified in Freund's Complete Adjuvant (FCA) (Sigma) subcutaneously for the first injection, and by intramuscular injection for two subsequent times using Freund's Incomplete Adjuvant (FIA) (Sigma). Balb/C mice were intraperitoneally immunized with 15 μg of GST-Bc28.2 emulsified in FCA for the first injection and in FIA for the two subsequent times. Injection of the animals was performed at 3-week intervals and the bleedings were done 8 days before each immunisation.

The rabbit α-His-Bc28.1C antiserum was used to reduce *Babesia* parasite invasion into erythrocytes, see Example 4.

2.1.3. Immunological Methods 2.1.3.1. Immunoblotting

Immunoblotting was performed with purified *B. canis* merozoites prepared as described in Drakulovski et al. (2003, Infect. Immun., vol. 71, p. 1056-1067). The merozoites were then processed for electrophoresis and the proteins were separated by 15% SDS-PAGE. Immunoblottings were revealed using a 1:100 dilution of the polyclonal serum α-His-Bc28.1C.

2.1.3.2. Indirect Immunofluorescence Assays (IFA)

IFA were performed on *B. canis* parasitised erythrocytes (5% of parasitaemia) as described in Drakulovski et al. (supra) using a 1:100 dilution for the polyclonal serum α-His-Bc28.1C. Slides were mounted with Citifluor® solution (Citifluor Ltd, London, UK) for limiting extinction fluorescence and the fluorescence was detected using a fluorescence microscope (Axioscope, Zeiss).

2.1.3.3. [$^{35}$S]-Methionine or [$^{3}$H]-Ethanolamine Radiolabeling of *B. canis* Culture and Immunoprecipitation

[$^{35}$S]-methionine radiolabeling of in vitro cultures of *B. canis* and immunoprecipitation experiments were performed as described in Drakulovski et al. (supra). Briefly, the [$^{35}$S]-methionine-radiolabeling was performed with 50 μCi/ml (1200 Ci/mmol, Amersham-Pharmacia Biotech) and a 5% starting parasitaemia. Fractions used from *B. canis* for immunoprecipitation experiments were: total, culture supernatant (SPA), infected-erythrocyte stroma, purified merozoite, Triton X-114 aqueous (soluble and hydrophilic antigens), and Triton X-114 detergent (insoluble and hydrophobic antigens) fractions, as source of radiolabeled antigens ($10^6$ cpm). The [$^{3}$H]-ethanolamine radiolabeling of the in vitro culture from *B. canis* was performed with 50 μCi/ml of radiolabeled component (25 μCi/mmol, Amersham-Pharmacia Biotech) with a 5% starting parasitaemia and immuno-precipitation experiments were performed with the total and SPA fractions as the source of [$^{3}$H]-ethanolamine radiolabeled antigens ($10^6$ cpm) from *B. canis*.

2.1.3.4. Protein Phase Separation by TX-114 Treatment

The proteins of *B. canis* from the [$^{35}$S]-methionine radiolabeled merozoite and infected erythrocyte stroma fractions were phase separated in Triton X-114 (Sigma) as described in Precigout et al. (1991, Infect. Immun., vol. 59, p. 2799-2805).

2.1.4. Erythrocyte Binding Assay

100 μg of His-Bc28.1 protein or His-GST (as a control) were purified under native condition according to the manufacturer's instructions (Qiagen). They were then incubated with 50 μl of canine red blood cells in 1 ml of PBS during 1 h at room temperature. Erythrocytes were harvested by centrifugation (2 min, 200×g) and resuspended in 200 μl of PBS. The suspension was then layered onto a 400 μl silicon oil cushion (Aldrich). After centrifugation (4 min, 3000×g), the supernatant and the silicon oil were discarded and the proteins bound to erythrocytes were eluted by 75 μl of 0.5 M of $PO_4$NaCl. Eluted proteins were resolved by SDS-PAGE and detected by an anti His-tag monoclonal antibody (Qiagen) at a 1/20.000 dilution in Western blot using the SuperSignal West Pico Chemoluminescent Substrate kit according to manufacturer's instructions (Pierce).

2.1.5. Analysis of Parasitic Antigens Localised on the Surface of B. canis-Infected Erythrocytes An in vitro culture of B. canis was firstly radiolabeled with [$^{35}$S]-methionine as previously described. Erythrocytes were then collected and were biotinylated in a solution of EZ link® sulfoLC NHS biotin (Pierce) (1M in PBS, pH 7.2) during 30 min at room temperature. Then, erythrocytes were washed three times with PBS and the biotinylated extract was passed on a silicone oil cushion (Aldrich), to eliminate lysed erythrocytes. After a centrifugation (20 min, 700×g), intact erythrocytes from the pellet were washed with PBS, lysed and processed for immunoprecipitation experiments as described in Drakulovski et al. (supra). Immunoprecipitations were performed with the α-His-Bc28.1C antiserum as previously described or with vaccinated/challenged serum. These vaccinated/challenged sera had been produced by giving dogs three vaccinations with an SPA, followed by a homologous challenge. Such sera had been produced for B. canis isolate A (α-A), isolate B (α-B), and B. rossi isolate F (α-F) parasites. The corresponding pre-immune dog sera were also tested as negative controls. Then, immunoprecipitated proteins were separated by SDS-PAGE and the gel, rather than to be treated for revelation of immunoprecipitation experiments, was blotted on a nitrocellulose membrane. Biotinylated proteins from the surface of erythrocytes were then revealed by incubating the membrane with a Streptavidin-POD component (Roche) at a 1/2000 dilution and by using the SuperSignal® West Pico Chemoluminescent Substrate kit according to the manufacturer's instructions (Pierce). Once the total biotinylated proteins from the surface of the red blood cells were revealed, the Western blot was autoradiographed on Biomax MR film (Eastman Kodak Co) in order to certify the parasitic origin of the biotinylated proteins.

2.1.5.1. Determination of the Strength of Erythrocyte-Membrane Binding

In an attempt to analyse if the potential surface antigens from B. canis immunoprecipitated by the α-His-Bc28.1C antiserum were only attached stuck on the surface of the erythrocytes rather than being a true surface integrated antigen, the strength of their interaction with the surface of infected erythrocytes was evaluated. Erythrocytes from an in vitro culture of B. canis were radiolabeled, biotinylated and passed through a silicon oil cushion, as previously described. Intact erythrocytes were collected, incubated with an equal volume of NaCl at a concentration varying from 0.5 to 2M during 2 min at room temperature. Then, the eluate was analysed in Western blot with the α-His-Bc28.1C or with the pre-immune rabbit serum as control.

2.2. Results

2.2.1. Biochemical Characterization of the Bc28.2 Protein

Figure 10:
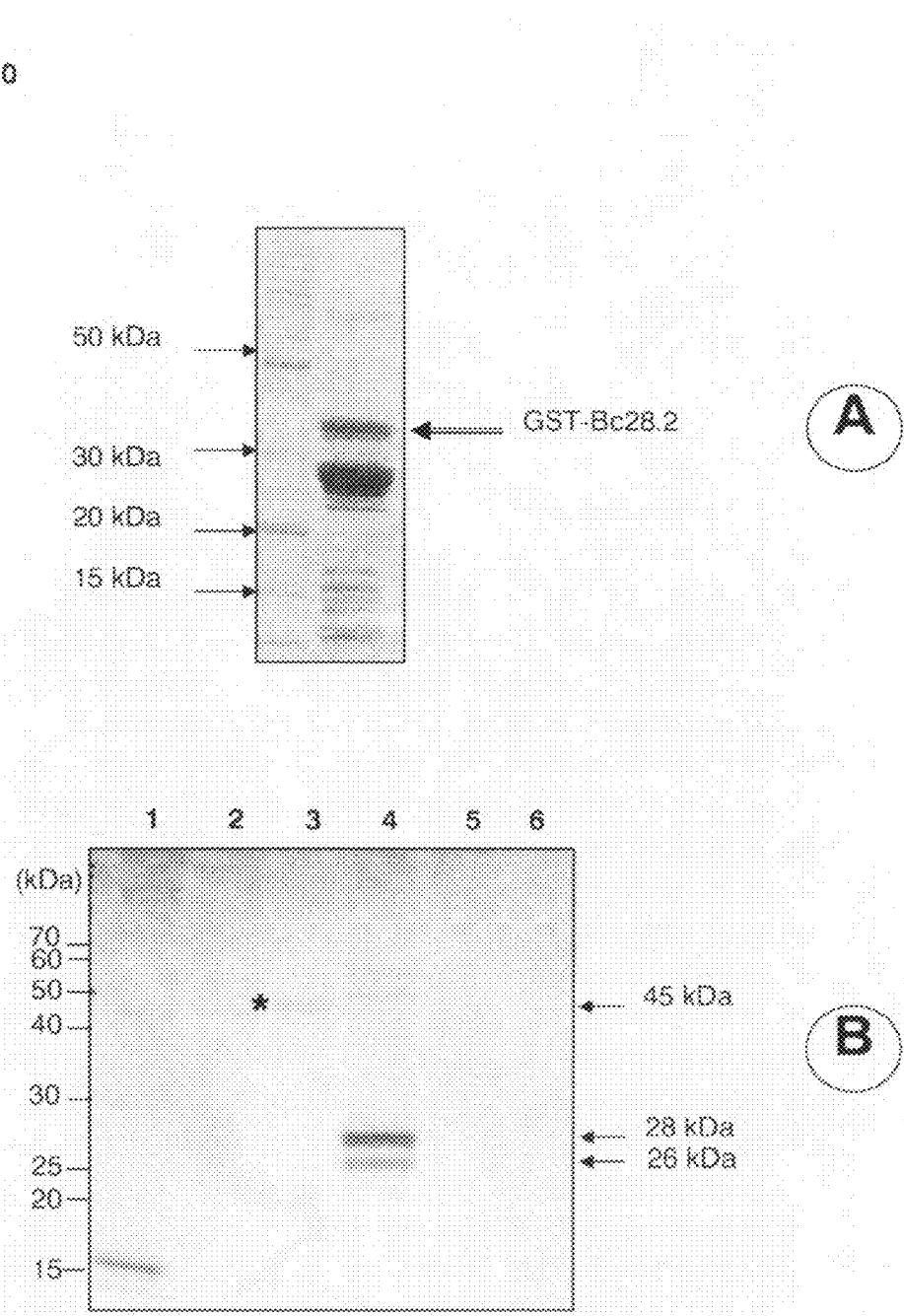

The 504 bp Bc28.2 clone, was cloned in the pGEX vector to produce a purified GST-Bc28.2 recombinant protein of around 35 kDa (FIG. 10, A) that was used to produce a polyclonal antibody in mice. This α-GST-Bc28.2 serum reacts weakly but specifically in immunoprecipitation with a 45 kDa protein in the total fraction (FIG. 10, B, lane 3, indicated by an asterisk). This 45 kDa protein was also detected by the serum in the merozoite fraction but not in the stroma and SPA fractions of B. canis (data not shown). As controls, an unrelated anti-GSTBcvir15 was reactive only with its 15 kDa protein (FIG. 10, B, lane 1) and the pre-immune sera were negative (FIG. 10, B, lanes 2 and 5). The 28/26 kDa doublet of proteins immunoprecipitated by the α-His-Bc28.1C were never immunoprecipitated by the α-GST-Bc28.2 serum. Similar results were obtained with isolate B of B. canis.

In conclusion: the α-GST-Bc28.2 serum reacts with a 45 kDa protein but not with the 28/26 kDa protein doublet recognized by the α-His-Bc28.1C serum.

2.2.2. Biochemical Characterization of the Bc28.1 Protein

Figure 12:
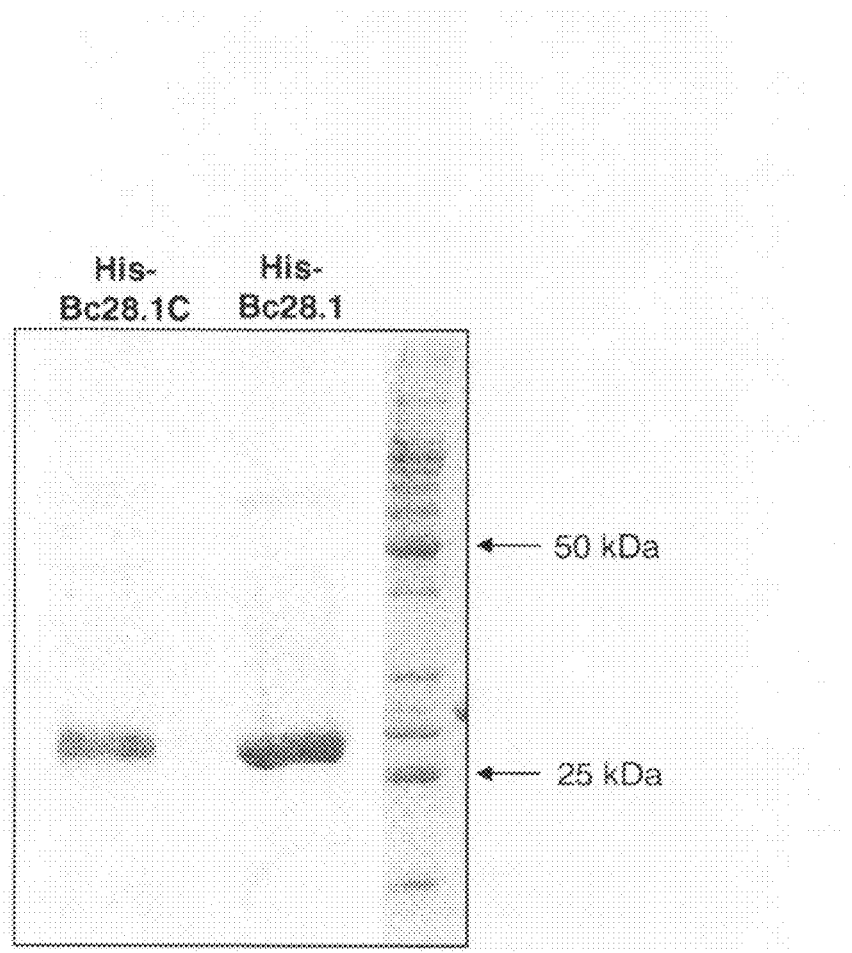

Two recombinant Histidine tagged-Bc28.1 proteins, without the N-terminal part of Bc28.1, but with or without the GPI anchor at the C-terminal part, designated His-Bc28.1C ($V^{16}$-$V^{256}$) and His-Bc28.1 ($V^{16}$-$K^{233}$) respectively, were purified (FIG. 12). The His-Bc28.1C protein was purified under denaturing conditions and was injected into a rabbit to produce a polyclonal serum (α-His-Bc28.1C). The His-Bc28.1 protein was purified under native conditions and was used for the erythrocyte binding assay (section 2.1.4).

2.2.2.1. The Bc28.1 Protein is a GPI Anchor Protein

A metabolic labelling of a B. canis lysate with [$^3$H]-ethanolamine, confirmed the GPI nature of the hydrophobic C-terminal peptide of Bc28.1 product since a single $^3$H labeled protein of 28 kDa was specifically immunoprecipitated with the α-His-Bc28.1 C serum (FIG. 13, C, lane 2). The pre-immune serum was unreactive (FIG. 13, C, lane 1).

2.2.3. Reactivities of the α-His-Bc28.1C Serum in Immunoprecipitation Assays

2.2.3.1. Reactivity on Total Antigens and Soluble Parasitic Antigen (SPA).

A doublet of 28/26 kDa was recognised in the total fraction of B. canis by the α-His-Bc28.1C serum but only the 26 kDa protein was detected in the supernatant, i.e. SPA fraction (FIG. 12, A, lanes 2). Moreover, this doublet of 28/26 kDa proteins corresponded to proteins that were specifically recognized by the anti-A vaccinated/challenged serum (FIG. 13, A, lanes 3). Pre-immune sera from rabbit or dog were unreactive (FIG. 13, A, lanes 1 and 4, respectively).

2.2.3.2. Reactivity on Fractionated Antigens

[$^{35}$S]-methionine radiolabeled parasitised red blood cells were lysed with streptolysin. The sample was centrifuged and the supernatant (erythrocyte stroma fraction) was collected. The pellet (merozoite mixed with ghost) was processed through a Percoll gradient to collect enriched fractions of purified radiolabeled merozoites (merozoite fraction). One part of the merozoite and infected erythrocyte stroma fractions was used for phase separation of the proteins in TX-114. Immunoprecipitation experiments with the α-His-Bc28.1C serum were performed using erythrocyte stroma and merozoite fractions and their corresponding TX-114 aqueous- (soluble antigens, indicated Aq.) and detergent- (insoluble antigens, indicated Det.) fractions, as sources of radiolabeled antigens of B. canis (FIG. 13, B).

This shows that the α-His-Bc28.1C serum (FIG. 13, B, lanes 2) detects the 28 kDa antigen in the merozoite fraction and that this protein is present in the detergent phase, suggesting it's an insoluble antigen (FIG. 13, B, lane Det). In contrast, the 26 kDa antigen is detected in the stroma of infected erythrocyte and this protein is present in the aqueous phase, suggesting it's a soluble protein (FIG. 13, B, lane Aq).

Similar results were obtained with the isolate B (data not shown).

2.2.4. Localization of the Bc28.1 Protein by Immunofluorescence Assays

The pattern of fluorescence of the α-His-Bc28.1C serum on fixed infected erythrocytes from the isolate A of B. canis (FIG. 13, D) shows a merozoite surface labelling (picture II, as indicated by an arrow). Moreover, a strong labelling of vesicles that are present in the stroma of the infected erythrocyte was also obtained (Picture I, indicated by an arrow on the tetrad form).

2.2.5. Recognition of Bc28.1 by a *B. rossi* Antiserum

A vaccination/challenge serum against *B. rossi*, isolate F, was used in immunoprecipitation of $^{35}$S labeled *B. canis* isolate B total antigens, which antigens had first been separated with TX-114 into a hydrophobic (detergent: Det.) and a hydrophilic (aqueous: Aq.) phase. This heterologous antiserum precipitated the 28 kDa form of Bc28.1 in the hydrophobic phase, and both the 26 and the 28 kDa form in the hydrophilic phase (FIG. 11, lanes 3 and 7), all visible just below the indicated 30 kDa marker band location. Positive and negative control antisera are included.

2.2.6. The Bc28.1 Protein Binds to Erythrocytes

The ability of the Bc28.1 protein to bind to the surface of infected erythrocytes was determined by performing an erythrocyte binding assay (FIG. 14, A). As presented in FIG. 14 (A, lane 2), the His-Bc28.1 protein was detected in Western blot by the anti-His monoclonal antibody, indicating that this protein is able to bind to canine erythrocytes. As control, no reactivity was observed when the test was performed with the unrelated His-GST (FIG. 14, A, lane 1).

2.2.7. The Bc28.1 Protein is an Erythrocyte Surface Antigen

Biotinylated intact erythrocytes, resulting from a [$^{35}$S]-methionine radiolabeling of an in vitro culture of *B. canis* (isolate A), were lysed and processed for immunoprecipitations experiments with vaccinated/challenged serum against the isolate A of *B. canis* (α-A) or with the α-His-Bc28.1C antiserum, and with their corresponding pre-immune sera. Immunoprecipitated proteins were separated by SDS-PAGE, the gel was blotted on a nitrocellulose membrane and biotinylated proteins from the surface of erythrocytes were revealed (FIG. 14, B, II). Once the total biotinylated proteins from the surface of the red blood cells were revealed, the Western blot was autoradiographed in order to certify the parasitic origin of the biotinylated proteins (FIG. 14, B, I). Whereas the α-His-Bc28.1C antiserum immunoprecipitated a 28/26 kDa doublet of proteins (FIG. 14, B, I, lane 2), this experiment showed that only the 28 kDa protein was biotinylated (FIG. 14, B, II, lane 2), indicating that the 28 kDa protein from the doublet is an integrated surface erythrocyte antigen of *B. canis*. This biotinylated 28 kDa protein was also immunoprecipitated by the α-A serum (FIG. 14, B, II, lane 3). Pre-immune sera were negative (FIG. 14, B, lanes 1 and 4).

2.2.7.1. Determination of the Strength of Erythrocyte-Membrane Binding

In an attempt to analyse if the 28.1 surface antigen from *B. canis* immunoprecipitated by the α-His-Bc28.1C antiserum was only attached to the surface of the erythrocytes rather than being associated with it, the strength of the interaction with the surface of infected erythrocytes was evaluated.

Radiolabeled and biotinylated intact erythrocytes were treated with an NaCl solution at a concentration varying from 0.5 to 2M. This showed the 28 kDa protein was not eluted from the surface of the erythrocyte even at a 2M concentration of NaCl. This proves that it is a true surface integrated antigen of *B. canis*.

In conclusion: the biochemical characterization of the Bc28.1 protein showed that the α-His-Bc28.1C serum recognized a 28/26 kDa doublet of proteins.

Both the 28 and 26 kDa proteins are recognized by immune serum of dogs infected by *B. canis*, suggesting that they are excellent candidates for a recombinant vaccine against infection with Babesiidae.

The data indicate that the 28 kDa is an insoluble protein with a GPI-anchor. The protein is associated with the surface of the merozoite and the infected erythrocyte. The 26 kDa protein is a soluble parasite antigen (SPA) that was identified in the infected erythrocytic and supernatant fractions. The characterisation of the 26 kDa protein as a secreted protein is in agreement with the presence of a cleavable peptide signal at the N-terminal part of the Bc28.1 protein and with the presence in vesicles within the erythrocytes stroma as detected by IFA.

Firstly, the data indicates that the Bc28.1 protein binds to erythrocytes, indicating an interaction of this protein with a ligand from the surface of the erythrocyte. As the 28 kDa product was demonstrated to be associated with the surface of the merozoite, it indicates that its infection of an erythrocyte involves this 28 kDa protein.

Secondly, the data shows also that the 28 kDa form is a surface located antigen. This analysis might also detect soluble antigen that attaches to the surface of infected erythrocytes. However, the fact that treatment of intact erythrocytes with a 2M solution of NaCl was unable to elute the Bc28.1 protein and that the biotinylated surface antigen detected is a 28 kDa protein (i.e. the form that is not a soluble antigen), proves that the 28 kDa form is firmly associated with the infected erythrocyte's outer membrane. This is indicative of a function of the protein in the binding and coagulation of (infected) erythrocytes. Indeed, agglutination of infected erythrocytes was already described for *B. canis* (Schetters et al., 1997, *Parasitology*, vol. 115, p. 485-493). Thus the infected erythrocyte's surface located 28 kDa protein binds to an (infected) erythrocyte component in order to form aggregates that enable the parasite to infect new erythrocytes without becoming exposed to the organism's immune system.

The two functions of the 28 kDa form of the Bc28.1 protein deduced from these data (i.e. invasion and coagulation) indicate that this protein plays a crucial role in the survival of the parasite. Indeed, these two mechanisms are essential for the parasite to evade the host immune system.

Example III

Vaccinations with Bc28.1 and Bc28.2 Protein Subunit Vaccines

3.1. Techniques Used

3.1.1. Animals

Male and female dogs, for instance Beagles of 6 months old, will be housed in the proper facilities. Several groups will be formed of appropriate size, based on random assignment. Blood samples will be taken before the start, and at several times during the experiment. The animal's general health will regularly be checked.

3.1.2. Vaccines

Bc28.1 and/or Bc28.2 protein will be produced for instance in a baculovirus expression vector system or in the Roche in vitro expression system. Proteins will be characterised through Western blots, quantitated preferably by an Elisa, and formulated, preferably with Quil A.

3.1.3. Vaccinations

Dogs will receive a single dose of vaccine, at two time points, with an interval of approximately three weeks. Injections will be subcutaneous.

At weekly interval blood samples will be drawn, to prepare serum, for serological analysis, preferably by Elisa.

At approximately two weeks after the second vaccination a challenge infection will be given, using an appropriate dose of live *B. canis* parasites.

Animals will be monitored for clinical signs of infection for a period of 14 days after challenge infection. Special attention will be given to behaviour, spleen size, size of lymph nodes, colour of the mucous membranes of mouth and eyelid, and the capillary refill time. Clinical scores will be expressed as a numeric value as described in Schetters et al., 1994 (Vet. Parasitol., vol. 52, p. 219-233).

During the challenge observation time, daily blood smears will be prepared from citrated blood, these will be stained, and the number of parasite-infected erythrocytes will be counted. Daily haematocrit measurements will also be made.

After 14 days of challenge infection, dogs will receive chemotherapeutic treatment with Carbesia®, to cure the infection.

Example IV

Reduction of Invasion by *Babesia* Parasites into Erythrocytes with Specific Antibodies A rabbit polyclonal antiserum was used to prove the capability of antibodies specific for Bc28.1 protein to significantly reduce the invasion of *Babesia* parasites into erythrocytes.

4.1. Techniques Used

Standard *Babesia* cultures on dog erythrocytes were performed as described (Schetters et al., 1994, supra).

α-His-Bc28.1C antiserum had been produced as described above (section 2.1.2). In that same experiment rabbit pre-immune serum was obtained, which does not react with Bc28.1 protein (see FIG. 13). These sera were added to *Babesia* parasite cultures, either pure, or mixed 1:1, in the following scheme:

Serum sample nr 1: pure α-His-Bc28.1C antiserum

Serum sample nr 2: α-His-Bc28.1C antiserum and pre-immune serum mixed 1:1

Serum sample nr 3: pure pre-immune serum.

Suspension cultures contained 1% (v/v) dog red blood cells of which 1% was infected with *Babesia canis* parasites.

To triplicates of such suspension cultures 1:10 volume of the serum samples was added (160 μl serum(-mix) to 1.44 ml of culture), resulting in a final amount of the specific α-His-Bc28.1C antiserum in the cultures of 10, 5 or 0% v/v.

The cultures with the sera were incubated overnight, after which blood smears were prepared to determine the level of parasitaemia, by counting the number of erythrocytes that were parasite-infected by microscopy.

4.2. Results

Figure 15:
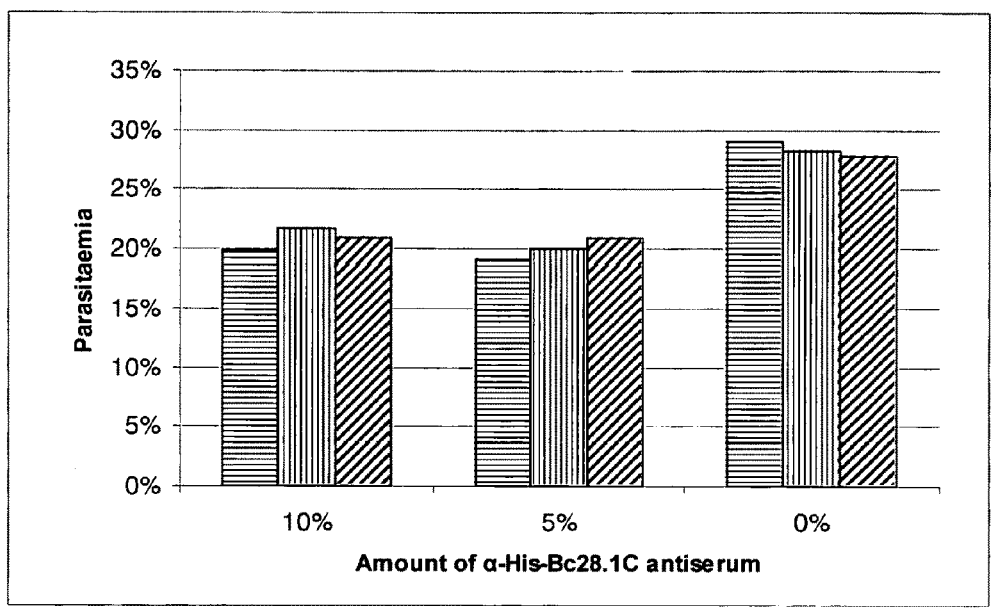

The results of the parasite invasion reduction assays are presented in Table 6, and depicted in the graph of FIG. 15. From this it is evident parasitaemia in erythrocyte-cultures containing α-His-Bc28.1C antiserum was significantly reduced in comparison to cultures with only a specific (pre-immune) rabbit serum. The reduction of the invasion amounted to 25%, as the level of parasite infected erythrocytes was reduced from 28 to 21%.

Even in the 1:1 diluted sample of α-His-Bc28.1C serum effectively this same level of invasion reduction was reached, see Table 6

TABLE 6 results of parasite-invasion reduction assays.

| Serum sample | Amount of α-His-Bc28.1C | Parasitaemia in triplicate cultures | | | Mean | St. dev. |
|---|---|---|---|---|---|---|
| | | A | B | C | | |
| 1 | 10% | 20% | 22% | 21% | 20.8% | 0.9% |
| 2 | 5% | 19% | 20% | 21% | 20.0% | 0.9% |
| 3 | 0% | 29% | 28% | 28% | 28.4% | 0.7% |

Legend to the Figures

FIG. 1: Amino acid alignment of Bc28.1 and Bc28.2 proteins

Identities between the two sequences are indicated by asterisks and homologies by single or double dots.

For Bc28.2, the signal peptide located at the N-terminal part, and for Bc28.1 the signal peptide and the GPI anchor located at the C-terminal part are bolded. Their cleavable sites are indicated by vertical arrows.

FIG. 2: Amino acid alignment of Bc28.1 proteins from geographically and genetically disparate *B. canis* field isolates.

Identities between the different sequences are indicated by asterisks and homologies by single or double dots.

The signal peptide located at the N-terminal part, and the GPI anchor located at the C-terminal part of the Bc28.1 proteins are bolded.

FIG. 3: Nucleotide sequence alignment of the nucleic acids encoding the Bc28.1 and Bc28.2 proteins according to the invention.

Identities between the two sequences are indicated by asterisks.

The positions of the initiation- and stop codons for the Bc28.1 and the Bc28.2 sequences are indicated; the corresponding nucleotides are bolded.

The location and 5'-3' orientation of primers derived from the Bc28.1 and Bc28.2 sequences are indicated by arrows and bolded; for pr 3 there is only a degenerated match.

FIG. 4: Nucleotide sequence alignment of the nucleic acids encoding the Bc28.1 protein from geographically and genetically disparate *B. canis* field isolates.

Identities between the two sequences are indicated by asterisks.

The position of the initiation and stop codon for each of the Bc28.1 sequences are indicated and bolded.

The location and 5'-3' orientation of primers are indicated by arrows.

FIG. 5: Identification of the partial Bc28.2 genomic DNA fragment from *B. canis*.

The Bc28.2 genomic DNA fragment was isolated by PCR with primer-couple pr 3 and E4 on genomic DNA from isolate A, of *B. canis* (lane 1). As negative controls, each of the primers pr 3 and E4 was also tested (lanes 2 and 3, respectively).

FIG. 6: Analysis of the specificity of reverse primers Rspe3C and Rspe3G for their respective Bc28.1 and potential Bc28.2 coding sequences.

PCR's were performed by using the A8 biological clone of *B. canis* as DNA template. The specificity of the reverse primer Rspe3C for the Bc28.1 coding sequence (I) and of the reverse primer Rspe3G for the potential Bc28.2 coding sequence (II) was tested by their use in a PCR reaction with the forward primer Cons3.1 (A) or with the forward primer Fspe3 (B). Amplimers resulting from these PCR reactions (lane PCR) were then digested with the restriction enzyme HinfI (H) or MstI (M). (C) Recapitulative scheme of the deduced restriction maps of the Bc28.1 coding sequence, partial genomic fragment Bc28.2 and Bc28.2 coding sequence.

FIG. 7: Molecular identification of the Bc28 multigene family by hybridisation experiment.

The PCR fragment FSpe3/Rspe4 from the Bc28.1 cDNA sequence was used as a probe for hybridisation experiments. (A) Southern blot of genomic DNA from the isolate A of *B. canis* digested with the restriction enzymes XbaI (lanes 1), XhoI (lanes 2), RsaI (lanes 3), NotI (lanes 4) and EcoRI (lanes 5). (B) Northern blot of total RNA from the isolate A of *B. canis*. (C and D) PFGE separation of entire (C) or NotI-digested (D) chromosomes of the isolates A and B of *B. canis*. (I) Ethidium bromide staining of the gel. (II) Corresponding gels hybridised with the Bc28.1 probe.

FIG. 8: Recapitulative scheme of comparative restriction maps of the Bc28.1 and Bc28.2 coding sequences.

(A) Comparative restriction maps of the Bc28.1 and Bc28.2 coding sequences between themselves within the biological clone A8 from *B. canis*. (B) Comparative restriction maps of the Bc28.1 coding sequence between geographically and genetically disparate *B. canis* field isolates. (C) Comparative restriction maps of the potential Bc28.2 coding sequence between geographically and genetically disparate *B. canis* field isolates. The restriction maps were performed on the basis of DNA digestion with AluI, EcoRI, HinfI, MboI and MspI.

FIG. 9: Predictive hydrophobicity profile of the Bc28.1 protein

The predicted N-terminal signal peptide and C-terminal GPI anchor are boxed.

FIG. 10: Identification of the protein encoded by the Bc28.2 coding sequence of *B. canis*

(A) SDS-PAGE of the purified GST-Bc28.2 recombinant protein. (B) Reactivity of the α-GST-Bc28.2 on protein extract from the total fraction of [$^{35}$S]-methionine radiolabelling of an in vitro culture of *B. canis* (isolate A). Immunoprecipitations were performed with the immune α-GST-Bcvir15 (lane 1), pre-immune α-GST-Bc28.2 (lane 2), immune α-GST-Bc28.2 (lane 3), immune α-His-Bc28.1 (lane 4), pre-immune α-His-Bc28.1 (lane 5) and immune α-His-Bd37 (lane 6) sera.

FIG. 11: Immunoprecipitations of hydrophilic and hydrophobic proteins of *B. canis*

Total, labeled (Aq.) and detergent-separated (Det.) antigens of *B. canis* isolate B were immunoprecipitated with: a vaccination/challenge serum directed against *B. canis* isolate A (α-A, lanes 1 and 5), an immune serum directed against *B. canis* isolate B (α-B, lanes 2 and 6), a vaccination/challenge serum directed against *B. rossi* isolate F (α-F, lanes 3 and 7), or an uninfected dog serum (N, lanes 4 and 8).

FIG. 12: Purification of recombinant His-Bc28.1 proteins.

SDS-PAGE of the purified recombinant His-Bc28.1C and His-Bc28.1 proteins. The His-Bc28.1C protein was purified under denaturing conditions whereas the His-Bc28.1 protein was purified under native conditions.

FIG. 13: Biochemical characterization of the Bc28.1 protein.

Immunoprecipitation experiments of [$^{35}$S]-methionine (A and B) or [$^3$H]-ethanolamine (C) radiolabeled antigens from *B. canis* (isolate A). Immunoprecipitations were performed with pre-immune α-His-Bc28.1C serum (lanes 1), immune α-His-Bc28.1C serum (lanes 2), immune α-A (from a dog vaccinated/challenged with the isolate A of *B. canis*) serum (lanes 3) and pre-immune α-A serum (lanes 4). Triton-X114 insoluble (Det.) and soluble (Aq.) antigens from the merozoite and stroma fractions were immunoprecipitated with the immune α-His-Bc28.1C serum. (D) Location of the Bc28.1 protein by immunofluorescence assays. Arrows respectively indicate the labelling of vesicles within the stroma of infected erythrocytes (picture I) and of the surface of the merozoite (picture II).

FIG. 14: Analysis of the erythrocyte binding property of the Bc28.1 protein and of the surface erythrocyte located antigens of *B. canis*.

Erythrocyte binding assays were performed both with 100 µg of purified His-Bc28.1 protein (lane 2) or His-GST (lane 1) that were incubated with canine red blood cells. The ability of each protein to bind to erythrocyte components was revealed by an anti His-tag monoclonal antibody (Qiagen) at a 1/120.000 dilution in Western blot. (B) Parasitic antigens localised on the surface of *B. canis*-infected erythrocytes were analysed by immuno-precipitation experiments with the α-His-Bc28.1C serum (lanes 1), immune α-His-Bc28.1C serum (lanes 2), immune α-A (from a dog vaccinated/challenged with the isolate A of *B. canis*) serum (lanes 3) and pre-immune α-A serum (lanes 4). Briefly, biotinylated and [$^{35}$S]-methionine radiolabeled intact erythrocytes were lysed and processed for immunoprecipitation experiments with the vaccinated/challenged serum against the isolate A of *B. canis* (α-A) or with the α-His-Bc28.1C antiserum, and with their corresponding pre-immune sera. Immunoprecipitated proteins were separated by SDS-PAGE, the gel was blotted on a nitrocellulose membrane and biotinylated proteins from the surface of erythrocytes were revealed (II). Once the total biotinylated proteins from the surface of the red blood cells were revealed, the Western blot was autoradiographed in order to certify the parasitic origin of the biotinylated proteins (I).

FIG. 15: Results of parasite-invasion reduction assays

Cultures of *Babesia canis* parasites on erythrocytes were incubated or not with different amounts of a polyclonal rabbit antiserum specific for protein His-28.1C. The resulting effect on the parasitaemia was determined by counting the relative number of parasite-infected erythrocytes by microscopy.

The invention claimed is:

1. An isolated amino acid sequence comprising amino acids 17 to 180 of SEQ ID NO: 2.

2. The sequence according to claim 1, comprising SEQ ID NO 2.

3. An isolated nucleic acid that encodes the sequence according to claim 1.

4. The nucleic acid according to claim 3 comprising SEQ ID NO: 1.

5. An isolated cDNA fragment comprising the nucleic acid according to claim 3.

6. A recombinant DNA molecule comprising the nucleic acid according to claim 3, under the control of a functionally linked promoter.

7. A live recombinant carrier comprising the nucleic acid according to claim 3.

8. A host cell comprising the nucleic acid according to claim 3.

9. A kit comprising the nucleic sequence of SEQ ID NO:1.

* * * * *

SEQUENCE LISTING

<160> NUMBER OF SEQ ID NOS: 19

<210> SEQ ID NO 1
<211> LENGTH: 852
<212> TYPE: DNA
<213> ORGANISM: Babesia canis

```
<220> FEATURE:
<221> NAME/KEY: CDS
<222> LOCATION: (50)..(820)

<400> SEQUENCE: 1
agtcgatacc tccgagaata gtcttgtatt aatcctgtcg ctattcaca atg aag ggt      58
                                                      Met Lys Gly
                                                        1 ttc ttc gga att att ttg tcc att att ttt gtt cgt gcc gtt agc tgc     106
Phe Phe Gly Ile Ile Leu Ser Ile Ile Phe Val Arg Ala Val Ser Cys
    5                  10                  15 act gag gat gag aaa agg gat agt gtc gtc gag ggc gct acg tcc gtt     154
Thr Glu Asp Glu Lys Arg Asp Ser Val Val Glu Gly Ala Thr Ser Val
 20                  25                  30                  35 gaa gcc agc tta aag gag cag atc gac tgg ctc gct gaa cgt tat tcc     202
Glu Ala Ser Leu Lys Glu Gln Ile Asp Trp Leu Ala Glu Arg Tyr Ser
                 40                  45                  50 gct gac ttg act aac aaa gac act tca aaa tgg aat acc gac gag aag     250
Ala Asp Leu Thr Asn Lys Asp Thr Ser Lys Trp Asn Thr Asp Glu Lys
             55                  60                  65 gtg aag gag ctg ttg aat gag aag gct gtt ggc ata gag tct cgc ctt     298
Val Lys Glu Leu Leu Asn Glu Lys Ala Val Gly Ile Glu Ser Arg Leu
         70                  75                  80 ctt gcc att gct aag gaa ttc cac aaa ttg aag tcc gtt ctg tgc acc     346
Leu Ala Ile Ala Lys Glu Phe His Lys Leu Lys Ser Val Leu Cys Thr
     85                  90                  95 ggc gtc aac gaa act ccc gct cat gtc gct aac agg gtg tca ccc gga     394
Gly Val Asn Glu Thr Pro Ala His Val Ala Asn Arg Val Ser Pro Gly
100                 105                 110                 115 gac gcc atc tcc atg ctc tac gtg ctt tct atc act cac agg gaa ttg     442
Asp Ala Ile Ser Met Leu Tyr Val Leu Ser Ile Thr His Arg Glu Leu
                 120                 125                 130 tct agc ctt aag aat aag atc gat gaa tgg aag aag gtc aag gca tct     490
Ser Ser Leu Lys Asn Lys Ile Asp Glu Trp Lys Lys Val Lys Ala Ser
             135                 140                 145 gaa gat ggc acc aaa gtg atc caa aat atc aag gac gac agg act aac     538
Glu Asp Gly Thr Lys Val Ile Gln Asn Ile Lys Asp Asp Arg Thr Asn
         150                 155                 160 acc tgg ttc gtt gcc cat gga ttc aag gta gct gag ctc aac gat gtc     586
Thr Trp Phe Val Ala His Gly Phe Lys Val Ala Glu Leu Asn Asp Val
     165                 170                 175 acc ctt gag aaa ctt gca aca gtg gtt aac gaa ttg gtg tcc cac aaa     634
Thr Leu Glu Lys Leu Ala Thr Val Val Asn Glu Leu Val Ser His Lys
180                 185                 190                 195 gat atg att tac att aac gac gct atg aag caa aac gtt gat aaa tgg     682
Asp Met Ile Tyr Ile Asn Asp Ala Met Lys Gln Asn Val Asp Lys Trp
                 200                 205                 210 acc aag gag gag tct gaa aga ttg gcc atg atg gct gaa cag ggt ata     730
Thr Lys Glu Glu Ser Glu Arg Leu Ala Met Met Ala Glu Gln Gly Ile
             215                 220                 225 tct gga gcc aag ggt aag aag gat gga ttc tca ttc gcc ggt ctt agt     778
Ser Gly Ala Lys Gly Lys Lys Asp Gly Phe Ser Phe Ala Gly Leu Ser
         230                 235                 240 gtc atc agc ctt ctt gtt gcc gcc gtc gcg gtt gtg gtc taa              820
Val Ile Ser Leu Leu Val Ala Ala Val Ala Val Val Val
     245                 250                 255 gaggttaagg atgactattt gtgggcgtaa tg                                  852

<210> SEQ ID NO 2
<211> LENGTH: 256
```

<212> TYPE: PRT
<213> ORGANISM: Babesia canis

<400> SEQUENCE: 2

```
Met Lys Gly Phe Phe Gly Ile Ile Leu Ser Ile Ile Phe Val Arg Ala
1               5                   10                  15

Val Ser Cys Thr Glu Asp Glu Lys Arg Asp Ser Val Val Glu Gly Ala
            20                  25                  30

Thr Ser Val Glu Ala Ser Leu Lys Glu Gln Ile Asp Trp Leu Ala Glu
        35                  40                  45

Arg Tyr Ser Ala Asp Leu Thr Asn Lys Asp Thr Ser Lys Trp Asn Thr
50                  55                  60

Asp Glu Lys Val Lys Glu Leu Leu Asn Glu Lys Ala Val Gly Ile Glu
65                  70                  75                  80

Ser Arg Leu Leu Ala Ile Ala Lys Glu Phe His Lys Leu Lys Ser Val
                85                  90                  95

Leu Cys Thr Gly Val Asn Glu Thr Pro Ala His Val Ala Asn Arg Val
            100                 105                 110

Ser Pro Gly Asp Ala Ile Ser Met Leu Tyr Val Leu Ser Ile Thr His
        115                 120                 125

Arg Glu Leu Ser Ser Leu Lys Asn Lys Ile Asp Glu Trp Lys Lys Val
130                 135                 140

Lys Ala Ser Glu Asp Gly Thr Lys Val Ile Gln Asn Ile Lys Asp Asp
145                 150                 155                 160

Arg Thr Asn Thr Trp Phe Val Ala His Gly Phe Lys Val Ala Glu Leu
                165                 170                 175

Asn Asp Val Thr Leu Glu Lys Leu Ala Thr Val Val Asn Glu Leu Val
            180                 185                 190

Ser His Lys Asp Met Ile Tyr Ile Asn Asp Ala Met Lys Gln Asn Val
        195                 200                 205

Asp Lys Trp Thr Lys Glu Glu Ser Glu Arg Leu Ala Met Met Ala Glu
210                 215                 220

Gln Gly Ile Ser Gly Ala Lys Gly Lys Lys Asp Gly Phe Ser Phe Ala
225                 230                 235                 240

Gly Leu Ser Val Ile Ser Leu Leu Val Ala Ala Val Ala Val Val
                245                 250                 255
```

<210> SEQ ID NO 3
<211> LENGTH: 845
<212> TYPE: DNA
<213> ORGANISM: Babesia canis
<220> FEATURE:
<221> NAME/KEY: CDS
<222> LOCATION: (2)..(784)

<400> SEQUENCE: 3

```
a gtc gat acc tcc gag aat agt ctt gta tta atc ctg tcg cta ttc aca      49
  Val Asp Thr Ser Glu Asn Ser Leu Val Leu Ile Leu Ser Leu Phe Thr
  1               5                   10                  15 atg aag ggt ttc ttc gga att att ttg tct att att ttc gtt cgt gcc       97
Met Lys Gly Phe Phe Gly Ile Ile Leu Ser Ile Ile Phe Val Arg Ala
            20                  25                  30 gtt agc tgc act gag gat gag aac agg gat agt gtc gtc gag ggc gct      145
Val Ser Cys Thr Glu Asp Glu Asn Arg Asp Ser Val Val Glu Gly Ala
        35                  40                  45 acg tcc gtt gaa gcc agc tta aag gag cag atc gac tgg ctc gct gaa      193
Thr Ser Val Glu Ala Ser Leu Lys Glu Gln Ile Asp Trp Leu Ala Glu
50                  55                  60
```

```
cgt tat tcc gct gac ttg act aac aaa gac act tca aaa tgg aat acc       241
Arg Tyr Ser Ala Asp Leu Thr Asn Lys Asp Thr Ser Lys Trp Asn Thr
 65                  70                  75                  80 gaa gag cag gtg aag gag ctg ttg aat gag aag gct gtt ggc ata gag       289
Glu Glu Gln Val Lys Glu Leu Leu Asn Glu Lys Ala Val Gly Ile Glu
                 85                  90                  95 tct cgc ctt ctt gcc att gct aag gag ttc cac aaa ttg aag tcc gtt       337
Ser Arg Leu Leu Ala Ile Ala Lys Glu Phe His Lys Leu Lys Ser Val
            100                 105                 110 ctg tgc acc ggc gtc aac gaa act ccc gct cat gtc gct aac agg gtg       385
Leu Cys Thr Gly Val Asn Glu Thr Pro Ala His Val Ala Asn Arg Val
        115                 120                 125 tca ccc gga gac gcc atc tcc atg ctt tac gtg ctt cct aac act cac       433
Ser Pro Gly Asp Ala Ile Ser Met Leu Tyr Val Leu Pro Asn Thr His
    130                 135                 140 agg gaa ttg tct agc ctt aag aat aag atc gat gaa tgg aag aag gtc       481
Arg Glu Leu Ser Ser Leu Lys Asn Lys Ile Asp Glu Trp Lys Lys Val
145                 150                 155                 160 aag gca tct gac aat ggc acc aat gtg atc aaa aat atc aag gac gac       529
Lys Ala Ser Asp Asn Gly Thr Asn Val Ile Lys Asn Ile Lys Asp Asp
                165                 170                 175 agg act aac acc tgg ttc gtt gcc cat gga ttc aag gta gct gag ctc       577
Arg Thr Asn Thr Trp Phe Val Ala His Gly Phe Lys Val Ala Glu Leu
            180                 185                 190 aac gat gta acc ctt gag aaa ctt gca aca gtg gtt aaa aaa ttg gtg       625
Asn Asp Val Thr Leu Glu Lys Leu Ala Thr Val Val Lys Lys Leu Val
        195                 200                 205 tcc cac aaa gat atg aaa tac att aac aaa gtt atg aaa aaa tat ttt       673
Ser His Lys Asp Met Lys Tyr Ile Asn Lys Val Met Lys Lys Tyr Phe
    210                 215                 220 gac agg cag aaa aag gag gct gaa aga ttg acc aaa aag gcc gag aag       721
Asp Arg Gln Lys Lys Glu Ala Glu Arg Leu Thr Lys Lys Ala Glu Lys
225                 230                 235                 240 ggt atg tct gga ggt aag tat aag gtg aaa ggt tat gca gcc ccc tct       769
Gly Met Ser Gly Gly Lys Tyr Lys Val Lys Gly Tyr Ala Ala Pro Ser
                245                 250                 255 act tgg atg cta tga ccatgcatac aagttgcaac taacaattaa cattttgaag       824
Thr Trp Met Leu
            260 cctgtactcc tcaatgagct c                                               845

<210> SEQ ID NO 4
<211> LENGTH: 260
<212> TYPE: PRT
<213> ORGANISM: Babesia canis

<400> SEQUENCE: 4

Val Asp Thr Ser Glu Asn Ser Leu Val Leu Ile Leu Ser Leu Phe Thr
 1               5                  10                  15

Met Lys Gly Phe Phe Gly Ile Ile Leu Ser Ile Ile Phe Val Arg Ala
                20                  25                  30

Val Ser Cys Thr Glu Asp Glu Asn Arg Asp Ser Val Val Glu Gly Ala
            35                  40                  45

Thr Ser Val Glu Ala Ser Leu Lys Glu Gln Ile Asp Trp Leu Ala Glu
        50                  55                  60

Arg Tyr Ser Ala Asp Leu Thr Asn Lys Asp Thr Ser Lys Trp Asn Thr
 65                  70                  75                  80

Glu Glu Gln Val Lys Glu Leu Leu Asn Glu Lys Ala Val Gly Ile Glu
```

```
                      85                  90                  95
Ser Arg Leu Leu Ala Ile Ala Lys Glu Phe His Lys Leu Lys Ser Val
            100                 105                 110
Leu Cys Thr Gly Val Asn Glu Thr Pro Ala His Val Ala Asn Arg Val
            115                 120                 125
Ser Pro Gly Asp Ala Ile Ser Met Leu Tyr Val Leu Pro Asn Thr His
            130                 135                 140
Arg Glu Leu Ser Ser Leu Lys Asn Lys Ile Asp Glu Trp Lys Lys Val
145                 150                 155                 160
Lys Ala Ser Asp Asn Gly Thr Asn Val Ile Lys Asn Ile Lys Asp Asp
                165                 170                 175
Arg Thr Asn Thr Trp Phe Val Ala His Gly Phe Lys Val Ala Glu Leu
                180                 185                 190
Asn Asp Val Thr Leu Glu Lys Leu Ala Thr Val Val Lys Lys Leu Val
                195                 200                 205
Ser His Lys Asp Met Lys Tyr Ile Asn Lys Val Met Lys Lys Tyr Phe
            210                 215                 220
Asp Arg Gln Lys Lys Glu Ala Glu Arg Leu Thr Lys Lys Ala Glu Lys
225                 230                 235                 240
Gly Met Ser Gly Gly Lys Tyr Lys Val Lys Gly Tyr Ala Ala Pro Ser
                245                 250                 255
Thr Trp Met Leu
            260

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
tgatgaagcc ggcaagaagg t                                               21

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
tacatgatac cgaattcaat gg                                              22

<210> SEQ ID NO 7
<211> LENGTH: 27
<212> TYPE: DNA
<213> ORGANISM: Artificial
<220> FEATURE:
<223> OTHER INFORMATION: Primer

<400> SEQUENCE: 7
ttacatcgtt gagctcagct accttga                                         27

<210> SEQ ID NO 8
<211> LENGTH: 22
<212> TYPE: DNA
<213> ORGANISM: Artificial
<220> FEATURE:
<223> OTHER INFORMATION: Primer
```

<400> SEQUENCE: 8
ccatggattc aaggtagctg ag                                           22

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
agtcgatacc tccgagaata g                                            21

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
actgaggatg agaacaggga tagt                                         24

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
catggattca aggtagctga g                                            21

<210> SEQ ID NO 12
<211> LENGTH: 24
<212> TYPE: DNA
<213> ORGANISM: Artificial
<220> FEATURE:
<223> OTHER INFORMATION: Primer

<400> SEQUENCE: 12
gaccacaacc gcgacggcgg caac                                         24

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
gagctcattg aggagtacag g                                            21

<210> SEQ ID NO 14
<211> LENGTH: 21
<212> TYPE: DNA
<213> ORGANISM: Artificial
<220> FEATURE:
<223> OTHER INFORMATION: Primer

<400> SEQUENCE: 14
cattacgccc acaaatagtc a                                            21

<210> SEQ ID NO 15
<211> LENGTH: 33

```
<212> TYPE: DNA
<213> ORGANISM: Artificial
<220> FEATURE:
<223> OTHER INFORMATION: Primer

<400> SEQUENCE: 15
attttggttc gtggatccac gtgcactgag gat                                  33

<210> SEQ ID NO 16
<211> LENGTH: 27
<212> TYPE: DNA
<213> ORGANISM: Artificial
<220> FEATURE:
<223> OTHER INFORMATION: Primer

<400> SEQUENCE: 16
ccacaaatag tcaagcttaa cctctaa                                         27

<210> SEQ ID NO 17
<211> LENGTH: 30
<212> TYPE: DNA
<213> ORGANISM: Artificial
<220> FEATURE:
<223> OTHER INFORMATION: Primer

<400> SEQUENCE: 17
gaatgagaat ccaagcttct tacccttggc                                      30

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18
cgactggagc acgaggacac tga                                             23

<210> SEQ ID NO 19
<211> LENGTH: 25
<212> TYPE: DNA
<213> ORGANISM: Artificial
<220> FEATURE:
<223> OTHER INFORMATION: Primer

<400> SEQUENCE: 19
gctgtcaacg atacgctacg taacg                                           25
```